US008685924B2

(12) United States Patent
Kamo

(10) Patent No.: US 8,685,924 B2
(45) Date of Patent: Apr. 1, 2014

(54) PREVENTIVES/REMEDIES FOR STRESS URINARY INCONTINENCE AND METHOD OF SCREENING THE SAME

(75) Inventor: Izumi Kamo, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/660,751

(22) PCT Filed: Aug. 24, 2005

(86) PCT No.: PCT/JP2005/015830
§ 371 (c)(1),
(2), (4) Date: Feb. 22, 2007

(87) PCT Pub. No.: WO2006/022420
PCT Pub. Date: Mar. 2, 2006

(65) Prior Publication Data
US 2007/0274913 A1    Nov. 29, 2007

(30) Foreign Application Priority Data
Aug. 25, 2004    (JP) ................. 2004-245931

(51) Int. Cl.
*A61P 13/10*   (2006.01)
*G01N 33/567*  (2006.01)

(52) U.S. Cl.
USPC ........... 514/15.4; 435/7.21; 530/834; 607/99; 607/118; 607/120

(58) Field of Classification Search
None
See application file for complete search history.

(56) References Cited

U.S. PATENT DOCUMENTS

| | | | |
|---|---|---|---|
| 5,744,474 | A | 4/1998 | Thor |
| 2003/0004207 | A1 | 1/2003 | Craig |

FOREIGN PATENT DOCUMENTS

| | | |
|---|---|---|
| JP | 62-267224 | 11/1987 |
| JP | 11-106334 | 4/1999 |
| JP | 2002-114684 | 4/2002 |
| JP | 2004-159919 | 6/2004 |
| JP | 2004-524029 | 8/2004 |
| WO | 96/10567 | 4/1996 |
| WO | 98/06404 | 2/1998 |
| WO | 98/33504 | 8/1998 |
| WO | 99/20279 | 4/1999 |
| WO | 99/52907 | 10/1999 |
| WO | 00/69437 | 11/2000 |
| WO | 00/76984 | 12/2000 |
| WO | 01/60352 | 8/2001 |
| WO | 02/08178 | 1/2002 |
| WO | 02/40457 | 5/2002 |
| WO | 02/47676 | 6/2002 |
| WO | 02/067867 | 9/2002 |
| WO | 02/083863 | 10/2002 |
| WO | 03/039553 | 5/2003 |
| WO | 03/072572 | 9/2003 |
| WO | 03/086306 | 10/2003 |
| WO | 03/097636 | 11/2003 |
| WO | 2004/000829 | 12/2003 |
| WO | 2004/000830 | 12/2003 |
| WO | 2004/096196 | 11/2004 |

OTHER PUBLICATIONS

Kamo et al., Am J Physiol Regul Integr Comp Physiol, 285(2): R356-365, May 15, 2003.*
Satoh et al., Neuroscience Research, 32(2):131-135, Oct. 1998.*
Kuo H-C, Urologia Internationalis, 69(1):36-41, Jan. 2002.*
Decramer et al., J Applied Physiol, 57(6): 1682-1687, Dec. 1984.*
Kamo et al., Am J Physiol Renal Physiol., 287:F424-F441, Apr. 27, 2004.*
M. Kitamura, Byoki to Kusuri (Disease and Medicine), Pharmacia, vol. 38, No. 7, pp. 665-667, 2002 (English translation).
R.H. P. Porter et al., "Functional Characterization of Agonists at Recombinant Human 5-HT$_{2A}$, 5-HT$_{2B}$ and 5-NT$_{2C}$ Receptors in CHO-K1 Cells", British Journal of Pharmacology, vol. 12, pp. 13-20, 1999.
Supplementary European Search Report dated Jul. 26, 2010, issued in corresponding European Application No. 05 78 1418.
Von Aase Hjorth et al., "Androgen in the treatment of urinary incontinence in elderly women", Gynaecologia International Monthly Review of Obsterics and Gynecology, vol. 142, No. 1, pp. 1-11 (1956).
J.A. Barsanti et al., "Testosterone Responsive Urinary Incontinence in a Castrated Male Dog", Journal of American Animal Hospital Association, vol. 17, No. 1, pp. 117-119 (1981).
W. D. Steers et al., "Effect of m-chlorophenylpiperazine on penile and bladder function in rats", American Journal of Physiology, vol. 257, No. 6, pp. 1441-1449, 1989.
D. C. M. Leysen, "Selective 5-HT$_{2C}$ agonists as potential antidepressants", I Drugs, vol. 2, No. 2, pp. 109-120, 1999.
M. Kitamura, Pharmacia, vol. 38, No. 7, pp. 665-667, 2002 (in Japanese).
A. S. Lin et al., "Effect of Simulated Birth Trauma on th Urinary Continence Mechanism in the Rat", Urology, vol. 52, No. 1, pp. 143-151, 1998.

(Continued)

*Primary Examiner* — Daniel E Kolker
*Assistant Examiner* — Stacey N MacFarlane
(74) *Attorney, Agent, or Firm* — Wenderoth, Lind & Ponack, L.L.P.

(57) ABSTRACT

An agent for the prophylaxis or treatment of stress urinary incontinence, which contains a substance that activates a serotonin 5-HT$_{2C}$ receptor, an agent for the prophylaxis or treatment of stress urinary incontinence, which contains a substance that stimulates an androgen binding site, and a method of screening for a drug for the prophylaxis or treatment of abdominal pressure incontinence, which includes electrostimulating the abdominal muscles or a nerve controlling them of an animal to increase the abdominal pressure, and measuring the leak point pressure at that time.

14 Claims, 1 Drawing Sheet

(56) References Cited

OTHER PUBLICATIONS

K. Sievert et al., "The Effect of Simulated Birth Trauma and/or Ovariectomy on Rodent Continence Mechanism. Part I: Functional and Structural Change", The Journal of Urology, vol. 166, pp. 311-317, Jul. 2001.

J. W. Thuroff et al., "Mechanisms of Urethral Continence: An Animal Model to Study Urethral Responses to Stress Conditions", The Journal of Urology, vol. 127, pp. 1202-1206, Jun. 1982.

H. Heidler et al., "Role of Striated Sphincter Muscle in Urethral Closure under Stress Conditions: An Experimental Study", Urol. Int., vol. 42, pp. 195-200, 1987.

I. Shimizu et al., "Pharmacological Effect of Amezinium on Urethra and Bladder of Rabbits", Int. Urogynecol. J., vol. 12, pp. 170-177, 2001.

I. Kamo et al., "Urethral Closure Mechanisms under Sneeze-Induced Stress Condition in rats: A New Animal Model for Evaluation of Stress Urinary Incontinence", American J Physiol. Reguratory Integrative Comp. Physiol., vol. 285, pp. 356-365, 2003.

M. J. Bishop et al., "New 5-$HT_{2C}$ Receptor Agonists", Expert Opinion Ther. Patents, vol. 13, No. 11, pp. 1691-1705, 2003.

S. R. Davis, "The role of Androgen Therapy", Best Practice & Research Clinical Endocrinology & Metabolism, vol. 17, No. 1, pp. 165-175, 2003.

R.H. P. Porter et al., "Functional Characterization of Agonists at Recombinant Human 5-$HT_{2A}$, 5-$HT_{2B}$ and 5-$HT_{2C}$ Receptors in CHO-K1 Cells", British Journal of Pharmacology, vol. 12, pp. 13-20, 1999.

Extended European Search Report issued Nov. 22, 2011 in corresponding European Application No. 11181877.9.

Hitoshi Kontani et al., "Effects of Adrenergic Agonists on an Experimental Urinary Incontinence Model in Anesthetized Rabbits", Japan J. Pharmacol., vol. 58, No. 4, Apr. 1, 1992, pp. 339-346.

J. Y. Lee et al., "The effects of periurethral muscle-derived stem cell injection on leak point pressure in a rat model of stress urinary incontinence", Int. Urogynecology J., vol. 14, No. 1, Feb. 1, 2003, pp. 31-37.

Anne M. Weber, "Leak Point Pressure Measurement and Stress Urinary Incontinence", Current Women's Health Reports, vol. 1, No. 1, Aug. 2001, pp. 45-52.

Izumi Kamo et al., "Involvement of reflex urethral closure mechanisms in urethral resistance under momentary stress condition induced by electrical stimulation of rat abdomen", Am. J. Physiol. Renal Physiol., vol. 293, No. 3, Sep. 1, 2007, pp. F920-F926.

Partial European Search Report issued Sep. 22, 2010, in corresponding European Application No. 10 17 4167, in the English language.

"Arena Pharmaceuticals Announces First Quarter 2004 Financial Results", Arena Pharmaceuticals, Inc., Internet Citation (2004).

Mealy et al., "Treatment of Metabolic Disorders: APD-356", Drugs of the Future 200408 ES, 29(8), p. 850 (2004).

Smith et al., "Discovery and Structure Activity Relationship of ($1R$)-8-Chloro-2,3,4,5-tetrahydro-1-methyl-1$H$-3-benzazepine (Lorcaserin), a Selective Serotonin 5-$HT_{2C}$ Receptor Agonist for the Treatment of Obesity", Journal of Medical Chemistry 51(2), pp. 305-313 (2008).

Extended European Search Report issued Feb. 8, 2011 in corresponding European Application No. 10174167.

Dirk C M Leysen, "Selective 5-$HT_{2C}$ agonists as potential antidepressants", IDrugs, 2(2), pp. 109-120, (1999).

Office Action issued Apr. 30, 2013 in corresponding Japanese Application No. 2011-049685, with English translation.

\* cited by examiner

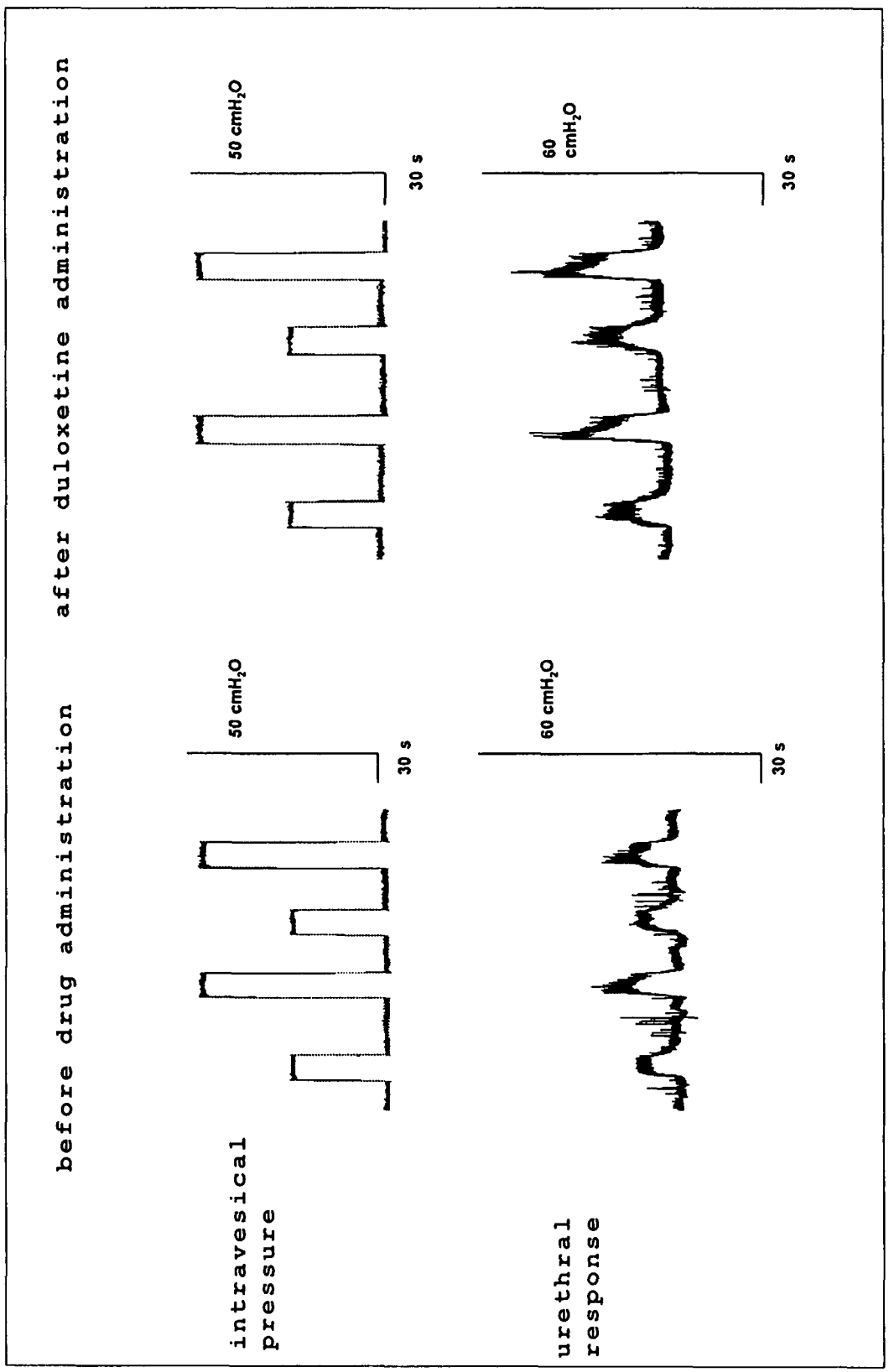

PREVENTIVES/REMEDIES FOR STRESS URINARY INCONTINENCE AND METHOD OF SCREENING THE SAME

This application is a U.S. national stage of International Application No. PCT/JP2005/015830 filed Aug. 24, 2005.

TECHNICAL FIELD

The present invention relates to an agent for the prophylaxis or treatment of stress urinary incontinence, which contains a substance that increases the leak point pressure during increase in abdominal pressure, and a method of screening for a drug for the prophylaxis or treatment of stress urinary incontinence, and the like.

BACKGROUND ART

The "stress urinary incontinence" is a disease characterized by a symptom of urine leakage when the abdominal pressure temporarily increases upon coughing, sneezing, straining or during light exercise such as going up and down the stairs and the like, or holding up a heavy luggage and the like, which is a disorder in the urinary continence mechanism. This disease is very common in women, and considered to occur because the pelvic floor muscles become weak due to birth and aging, and anatomical positions of pelvic organs including the bladder and urethra change (see, for example, "The Journal of Family Practice", 1982, vol. 14, p. 935-936). When the intravesical pressure increases due to an abrupt increase in the abdominal pressure, it is considered that the abdominal pressure passively transmits to the bladder and urethra, as well as the pelvic floor muscles and external urethral sphincter muscle actively contract via the nerve system to maintain urinary continence (see, for example, "The Journal of Urology", 1982, vol. 127, p. 1202-1206). Weakening of the pelvic floor muscles and external urethral sphincter muscle due to birth and aging is considered to be one cause of stress urinary incontinence, and it has been reported that the patients with stress urinary incontinence possibly have a defects in the reflex urinary continence mechanisms (see, for example, "British Journal of Urology", 1994, vol. 73, p. 413-417).

In mammals inclusive of human, when the urinary continence mechanism is intact, urine leakage due to an increase in the intravesical pressure associated with an abrupt increase in the abdominal pressure can be avoided by the function of the competing reflex increase in the intraurethral pressure. On the other hand, when, for example, a defect is present in a part of the urinary continence mechanism, for example, a defect in the neural systems involved in the guarding reflexes and a decrease in the contractile force of muscles involved in intraurethral pressure increase and the like, reflex increase in the intraurethral pressure cannot resist an increase in the intravesical pressure caused by an abrupt increase in the abdominal pressure, and urine leakage occurs. For screening for a therapeutic drug for stress urinary incontinence, therefore, an evaluation system reflecting such pathology is important.

Since many of human patients with stress urinary incontinence are parous women, and the frequency thereof increases in the postmenopausal period, external injury due to the delivery and decreased female hormone are held responsible therefore. As the situation stands, model rats are prepared using female rats as animals and based on vaginal expansion of parous rats and virgin rats, ovary removal, or combination of these (see, for example, "Urology", 1998, vol. 52, p. 143-151, and "The Journal of Urology", 2001, vol. 166, p. 311-317). As an evaluation parameter for the clinical diagnosis of stress urinary incontinence, the leak point pressure showing the urethral resistance in the urinary storage period is used. In animal experiment, it is a general method to gradually inject saline into the bladder under conditions free of the reflex voiding and measure the intravesical pressure at the time point of saline leakage from the uretral orifice (modified leak point pressure), or electrostimulate the abdominal wall or induce a sneeze by stimulating the mucous surface of the nasal cavity with a whisker when a half volume of the bladder is filled to increase the intravesical pressure, and observe the presence or absence of urine leakage (see, for example, "Urology", 1998, vol. 52, p. 143-151, and "The Journal of Urology", 2001, vol. 166, p. 311-317). However, in the former measurement, the increase in the intravesical pressure is persistent and gradual, and therefore, is not entirely considered to reflect the abrupt increase in the intravesical pressure that induces stress urinary incontinence. In the latter measurement, merely the presence or absence of stress urinary incontinence is detected, and the measurement is not entirely considered to quantitatively show the level of pathology. While a method including inducing a sneeze in anesthetized rats and measuring the sneeze leak point pressure at that time has also been reported (see, for example, "American Journal of Physiology-Regulatory, Integrative and Comparative Physiology", 2003, vol. 285, p. R356-R3656), the degree of increase in the intravesical pressure depends on the size of sneeze, which is difficult to control. A report has documented that an anesthetized dog is made to sneeze and the intraurethral pressure and the like are measured for the purpose of examining the mechanism of urinary continence maintenance (see, for example, "The Journal of Urology", 1982, vol. 127, p. 1202-1206, and "Urologia internationalis", 1987, vol. 42, p. 195-200). In these reports, however, changes in the topical pressure in a portion of urethra are measured, and the resistance of the whole urethra during increase in the abdominal pressure is not evaluated.

In addition, a method including electrostimulating an animal and measuring only the presence or absence of urine leakage has been reported (see "International Urogynecology Journal", 2001, vol. 12, p 170-177).

In small mammals, moreover, a screening method for a drug for the prophylaxis or treatment of stress urinary incontinence, which comprises measuring reflex contractile force of the pelvic floor muscles based on the intraurethral pressure has been reported (see JP-A-2004-159919).

There are many known compounds that bind to a serotonin 5-$HT_{2C}$ eceptor. WO02/040457, WO02/083863, WO03/097636, WO04/000829, WO04/000830, and WO02/008178 describe that a compound that bind to a serotonin 5-$HT_{2C}$ receptor is useful for the treatment of urinary incontinence and the like. However, they do not describe a treatment effect on the stress urinary incontinence.

WO99/20279 describes that a serotonin uptake inhibitor is useful for the treatment of urinary incontinence.

JP-A-7-188003 describes that duloxetine, which is a serotonin uptake inhibitor, is useful for the treatment of urgency incontinence and stress incontinence.

DISCLOSURE OF THE INVENTION

For screening for a novel therapeutic drug for stress urinary incontinence, development of a convenient, useful and efficient in vivo evaluation system is an important object. However, an efficient evaluation system wherein the leak point pressure due to an increase in the intravesical pressure based on an abrupt increase in the abdominal pressure is measured in animals has not been established at present except for a sneeze leak point pressure. As to the sneeze leak point pressure, however, since induction of sneeze and control of the degree of increase in the intravesical pressure are difficult, it is not a convenient method suitable for screening.

Once a new evaluation system capable of efficiently screening for a drug for treating stress urinary incontinence is established, a superior therapeutic drug for stress urinary incontinence can be provided.

The present inventors have conducted intensive studies in an attempt to solve the above-mentioned problems and, as a result, enabled measurement of leak point pressure by inducing urine leakage by increasing the intravesical pressure via elevation of abdominal pressure caused by electrostimulation of the abdominal wall of anesthetized female rats. Since the leak point pressure caused by electrostimulation of the abdominal wall remarkably decreases by bilateral transection of the pelvic nerves, including the sensory nerve from the bladder, they have found that the evaluation parameter involves a reflex urethral contraction responses caused by bladder compression and introduction of this evaluation parameter leads to the provision of a new in vivo efficient evaluation method of a drug for treating stress urinary incontinence. Moreover, using the in vivo efficient evaluation method and the like, the present inventors have found that a substance that activates a serotonin 5-$HT_{2C}$ receptor and androgen increase the urethral resistance, and can prevent or treat stress urinary incontinence. Based on these findings, the present inventors have further studied and completed the present invention.

Accordingly, the present invention provides the following:

[1] an agent for the prophylaxis or treatment of stress urinary incontinence, which comprises a substance that activates a serotonin 5-$HT_{2C}$ receptor,

[2] the agent of the above-mentioned [1], wherein the substance that activates a serotonin 5-$HT_{2C}$ receptor is a serotonin 5-$HT_{2C}$ receptor agonist,

[3] an agent for the prophylaxis or treatment of stress urinary incontinence, which comprises a substance that stimulates an androgen binding site,

[4] a method for the prophylaxis or treatment of stress urinary incontinence, which comprises administering, to a mammal, an effective amount of a substance that activates a serotonin 5-$HT_{2C}$ receptor,

[5] the method of the above-mentioned [4], wherein the substance that activates a serotonin 5-$HT_{2C}$ receptor is a serotonin 5-$HT_{2C}$ receptor agonist,

[6] a method for the prophylaxis or treatment of stress urinary incontinence, which comprises administering an effective amount of a substance that stimulates an androgen binding site,

[7] use of a substance that activates a serotonin 5-$HT_{2C}$ receptor, for the production of an agent for the prophylaxis or treatment of stress urinary incontinence,

[8] use of the above-mentioned [7], wherein the substance that activates a serotonin 5-$HT_{2C}$ receptor is a serotonin 5-$HT_{2C}$ receptor agonist,

[9] use of a substance that stimulates an androgen binding site, for the production of an agent for the prophylaxis or treatment of stress urinary incontinence,

[10] a method of screening for a substance that increases the leak point pressure during abdominal pressure increase, which comprises electrostimulating the abdominal muscle or diaphragm or a nerve controlling them of an animal to increase the abdominal pressure, and measuring the leak point pressure at that time,

[11] a method of screening for a drug for the prophylaxis or treatment of stress urinary incontinence, which comprises electrostimulating the abdominal muscle or diaphragm or a nerve controlling them of an animal to increase the abdominal pressure, and measuring the leak point pressure at that time,

[12] the method of the above-mentioned [10] or [11], wherein the leak point pressure is low during elevation of abdominal pressure,

[13] the method of the above-mentioned [12], wherein the low leak point pressure during increase in abdominal pressure is based on the transection or injury of the nerve involved in the reflex contraction of pelvic floor muscles or external urethral sphincter muscle, birth, ovariectomy, mechanical vaginal expansion treatment, diabetes, drug administration or combination of these, and

[14] the method of the above-mentioned [10] or [11], wherein the animal is female.

BRIEF DESCRIPTION OF THE DRAWINGS

FIG. 1 shows a typical example of the action of duloxetine on the urethral contractile responses induced by an increased intravesical pressure in urethane-anesthetized female rats.

BEST MODE FOR EMBODYING THE INVENTION

The present invention is explained in detail in the following.

A substance used for the agent for the prophylaxis or treatment of stress urinary incontinence of the present invention (hereinafter to be abbreviated as the substance of the present invention) increases the urethral resistance during elevation of abdominal pressure.

A substance that increases the urethral resistance during increment of abdominal pressure, for example, a substance that increases the leak point pressure, which shows urethral resistance, during abdominal pressure increase, and can be obtained using the below-mentioned screening method of the present invention and the like. Examples thereof include a substance that potentiates reflex contraction of the pelvic floor muscles and the urethra, a substance that increases the weight of the pelvic floor muscle groups and the urethra and the like.

More specifically, preferable substance used for the agent for the prophylaxis or treatment of stress urinary incontinence of the present invention includes a substance that activates a serotonin 5-$HT_{2C}$ receptor, a substance that stimulates an androgen binding site and the like.

The substance that activates a serotonin 5-$HT_{2C}$ receptor includes, for example, serotonin 5-$HT_{2C}$ receptor agonists (including partial agonists) and serotonin 5-$HT_{2C}$ receptor partial antagonists, and serotonin 5-$HT_{2C}$ receptor agonists (particularly full-agonist) are particularly preferably used.

The serotonin 5-$HT_{2C}$ receptor agonists more preferably have an inhibitory activity as shown by, for example, a 50% inhibitory concentration ($IC_{50}$) by a binding test of not more than about 1000 nM, preferably not more than about 100 nM. Specifically, as a serotonin$_{2C}$ receptor agonist, the compounds described in EP0572863, EP0863136, EP1213017, U.S. Pat. No. 3,253,989, U.S. Pat. No. 3,676,558, U.S. Pat. No. 3,652,588, U.S. Pat. No. 4,082,844, U.S. Pat. No. 4,971,969, U.S. Pat. No. 5,494,928, U.S. Pat. No. 5,646,173, U.S. Pat. No. 6,310,208, WO97/42183, WO98/30546, WO98/30548, WO98/33504, WO99/02159, WO99/43647 (U.S. Pat. No. 6,281,243), WO00/12475 (U.S. Pat. No. 6,380,238), WO00/12502 (U.S. Pat. No. 6,365,598), WO00/12510 (U.S. Pat. No. 6,433,175), WO00/12475, WO00/12481 (U.S. Pat. No. 6,552,062), WO00/12482, WO00/12502, WO00/16761, WO00/17170, WO00/28993, WO00/35922 (U.S. Pat. No. 6,372,745), WO00/44737, WO00/44753, WO00/64899, WO00/77001, WO00/77002, WO00/77010, WO00/76984 (U.S. Pat. No. 6,465,467), WO01/09111, WO01/09122, WO01/09123 (U.S. Pat. No. 6,638,936), WO01/09126, WO01/12602, WO01/12603 (U.S. Pat. No. 6,706,750), WO01/40183, WO01/66548 (U.S. Pat. No. 6,583,134), WO01/70207, WO01/70223, WO01/72752 (U.S. Pat. No. 6,734,301), WO01/83487, WO02/04456, WO02/04457, WO02/08178, WO02/10169, WO02/24700, WO02/24701, WO02/36596, WO02/40456, WO02/40457, WO02/42304, WO02/44124(U.S. Pat. No. 6,479,534), WO02/48124, WO02/51844 (U.S. Pat. No. 6,610,685), WO02/59124, WO02/59127, WO02/59129, WO02/72584, WO02/74746, WO02/83863, WO02/98350, WO02/98400, WO02/98860, WO03/00663, WO03/00666, WO03/04501, WO03/06466, WO03/11281, WO03/14118, WO03/14125, WO03/24976, WO03/28733, WO03/33497, WO03/57161, WO03/57213, WO03/57673, WO03/57674, WO03/62205, WO03/64423, WO03/86306, WO03/87086, WO03/89409, WO03/91250, WO03/91251, WO03/91257, WO03/97636, WO04/00829, WO04/00830 (U.S. Pat. No. 6,667,303), WO04/56324, WO04/78718, WO04/81010, WO04/087156, WO04/87662, WO04/87692, WO04/89897, WO04/096196, WO04/96201, WO04/112769, US2004192754, WO05/00849, WO05/03096, EP1500391, WO05/16902, WO05/19180, US2005080074, WO05/40146, WO05/41856, WO05/42490, WO05/42491, WO05/44812 and the like are used. Of these, particularly, the compounds described in (1) WAY-161503

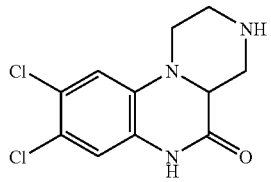

(2) m-CPP

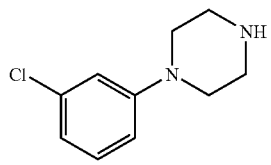

(3) PNU-22394A

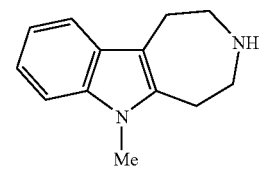

(4) Ro60-0175

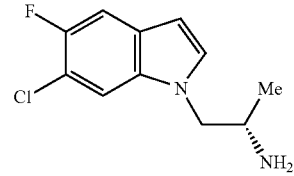

(5) ORG-12962

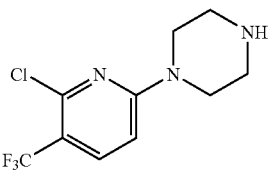

(6) Nordexfenfluramine

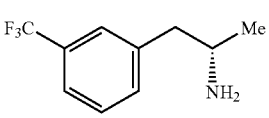

(7) MK-212

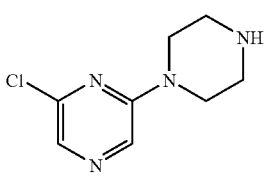

(8) Oxaflozane

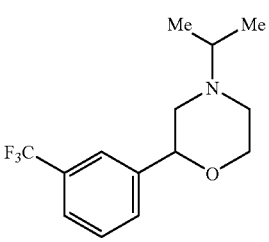

(9) a compound represented by the following structural formula described in WO00/12510 (U.S. Pat. No. 6,433,175)

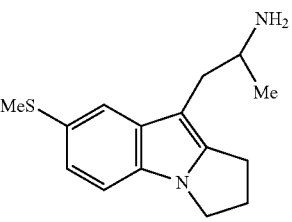 [SMILES: CSc1ccc2c(c1)c(CC(C)N)c1n2CCC1]

(10) a compound represented by the following structural formula described in WO02/51844 (U.S. Pat. No. 6,610,685)

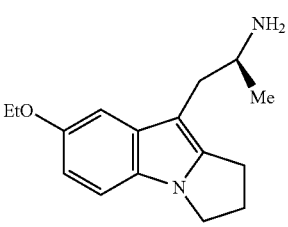 [SMILES: CCOc1ccc2c(c1)c(C[C@H](C)N)c1n2CCC1]

(11) a compound represented by the following structural formula described in WO01/66548 (U.S. Pat. No. 6,583,134)
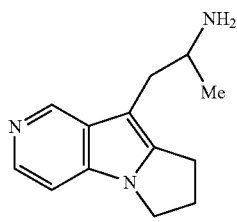 [SMILES: CC(N)Cc1c2n(c3ccncc13)CCC2]
(12) a compound represented by the following structural formula described in WO00/12482
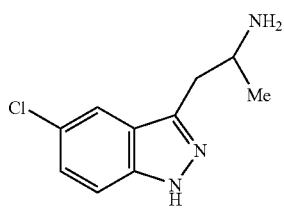 [SMILES: CC(N)Cc1n[nH]c2ccc(Cl)cc12]
(13) a compound represented by the following structural formula described in WO03/24976
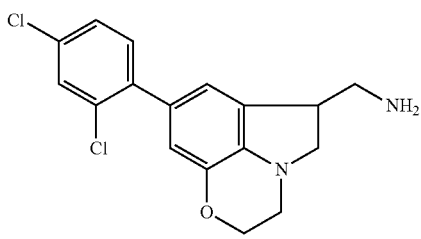
(14) ALX-2218
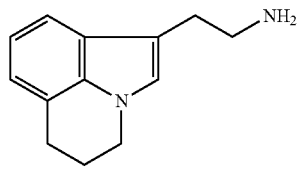
(15) ALX-2226
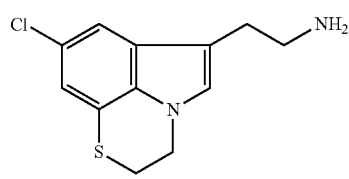
(16) Ro60-0332
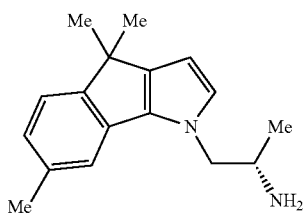
(17) VER-2692
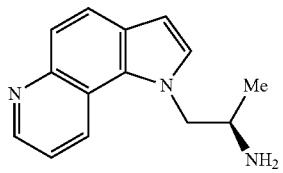
(18) VER-6925
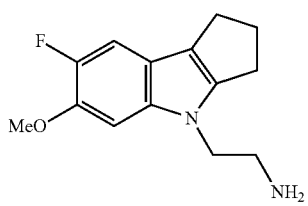
(19) VER-7397
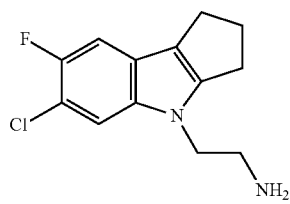
(20) VER-7499
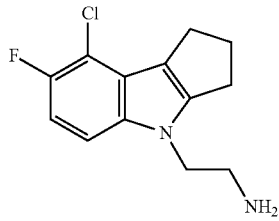
(21) VER-7443
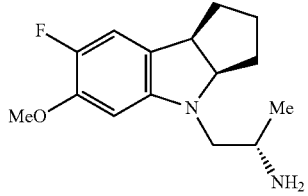
(22) VER-3993
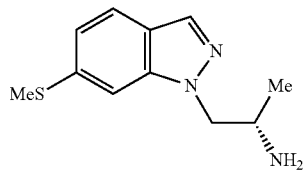
(23) YM-348
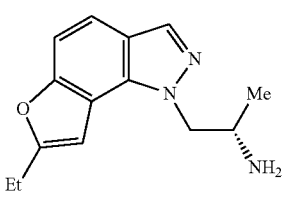

(24) a compound represented by the following structural formula described in WO03/57213.

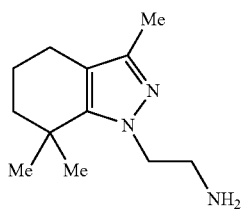 [SMILES: Cc1nn(CCN)c2c1CCCC2(C)C]

(25) a compound represented by the following structural formula described in WO03/57674

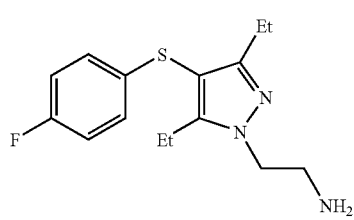 [SMILES: CCc1nn(CCN)c(CC)c1Sc1ccc(F)cc1]

(26) a compound represented by the following structural formula described in WO02/98860

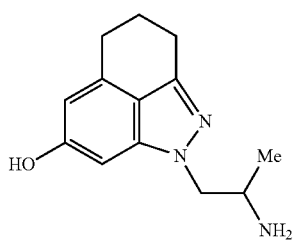
VER-5593

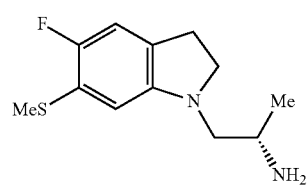
(28) VER-5384

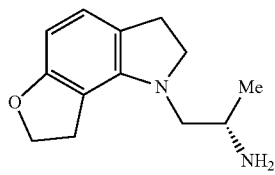
(29) VER-3323

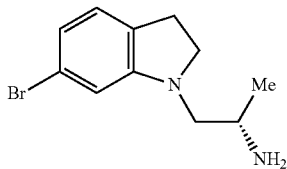

(30) a compound represented by the following structural formula described in WO02/44152 (U.S. Pat. No. 6,479,534)

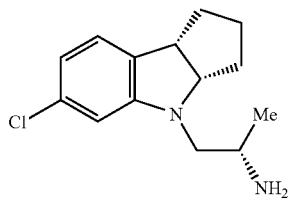 [SMILES: C[C@H](N)CN1c2cc(Cl)ccc2[C@@H]2CCC[C@@H]21]

(31) a compound represented by the following structural formula described in WO0/44737

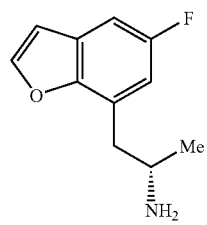 [SMILES: C[C@H](N)Cc1cc(F)cc2ccoc12]

(32) APD-356
(33) AR-10A
(34) a compound represented by the following structural formula described in WO02/40456

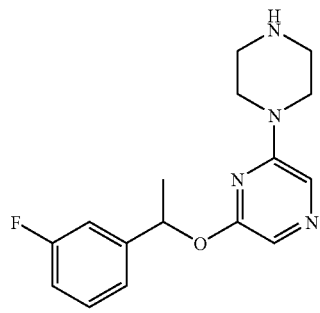 [SMILES: CC(Oc1cncc(N2CCNCC2)n1)c1cccc(F)c1]

(35) BVT-933
(36) a compound represented by the following structural formula described in WO02/08178

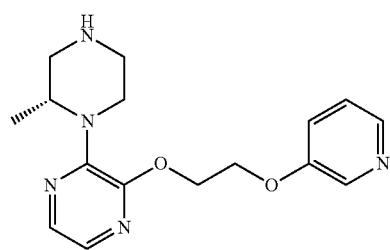

(37) PNU-243922

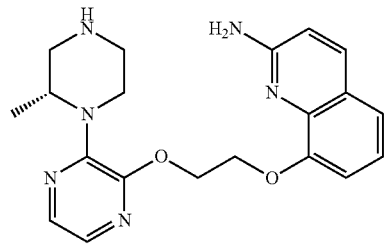

(38) a compound represented by the following structural formula described in WO03/00666

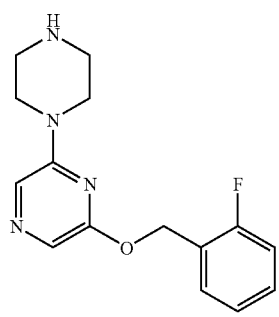 [SMILES: Fc1ccccc1COc1cncc(N2CCNCC2)n1]

(39) a compound represented by the following structural formula described in WO01/09123 (U.S. Pat. No. 6,638,936)

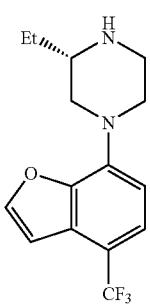

(40) a compound represented by the following structural formula described in WO01/09122

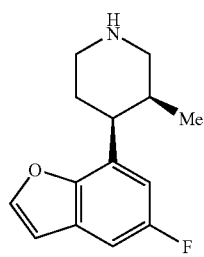 [SMILES: C[C@@H]1CNCC[C@@H]1c1cc(F)cc2ccoc12]

(41) a compound represented by the following structural formula described in WO01/09126

(42)

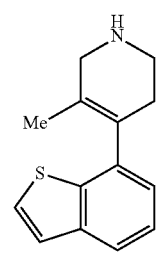

Org-37684

(43)

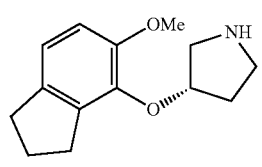

Org-36262 (Ro60-0527)

(43) Org-36262 (Ro60-0527)

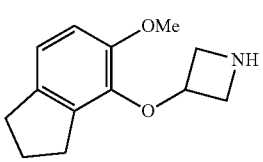

(44) a compound represented by the following structural formula described in EP0572863

(45)

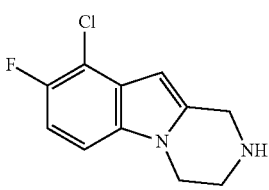

Ro60-0017 (Org-35013)

(46)

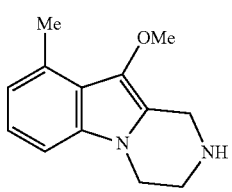

VER-3881

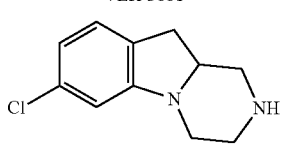

(47) a compound represented by the following structural formula described in WO02/72584

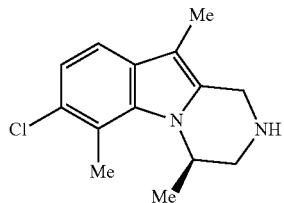

(48) Ro0721256

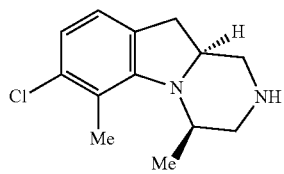

(49) PNU-181731A

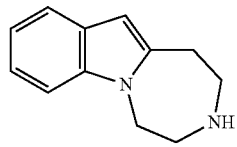

(50) a compound represented by the following structural formula described in WO02/59127

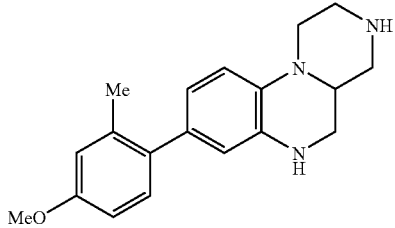 [SMILES: COc1ccc(-c2ccc3c(c2)NCC2CNCCN32)c(C)c1]

(51) a compound represented by the following structural formula described in WO03/14118

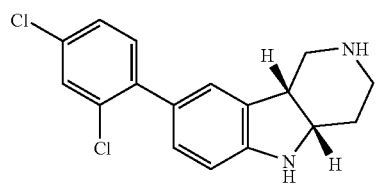 [SMILES: Clc1ccc(-c2ccc3c(c2)[C@@H]2CNCC[C@@H]2N3)c(Cl)c1]

(52) a compound represented by the following structural formula described in WO03/33497

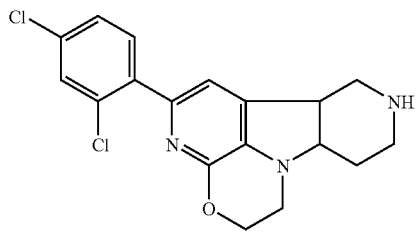

(53) IL-639

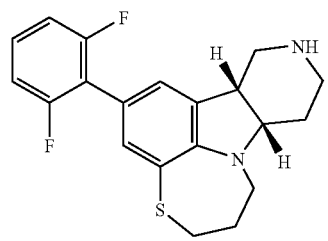

(54) IK-264

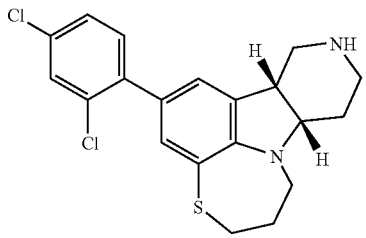

(55) VR-1065
(56) Ro60-0759

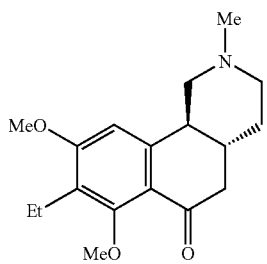

(57) Ro60-0869

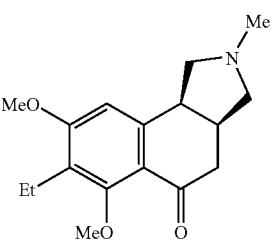

(58) a compound represented by the following structural formula described in WO00/64899

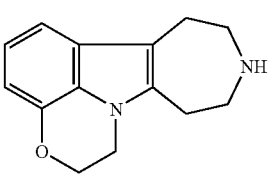

(59) PNU-57378E

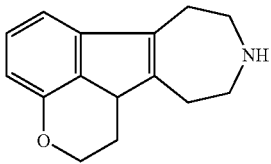

(60) a compound represented by the following structural formula described in WO03/06466

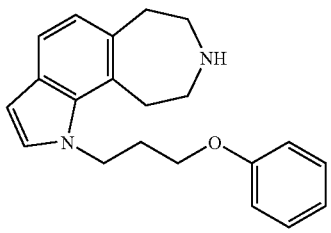 [SMILES: c1ccc(OCCCn2ccc3ccc4c(c32)CCNCC4)cc1]

(61) a compound represented by the following structural formula described in WO02/74746

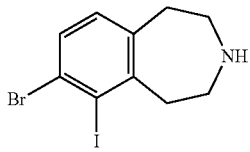

(62) a compound represented by the following structural formula described in WO02/42304

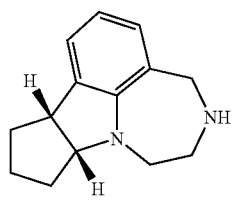

(63) WAY-470

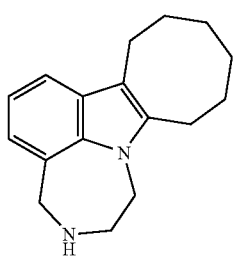

(64) WAY-629

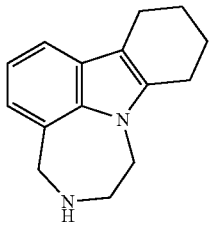

(65) a compound represented by the following structural formula described in WO97/42183

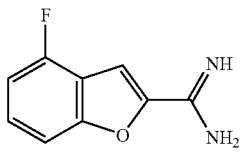 [SMILES: N=C(N)c1cc2c(F)cccc2o1]

(66) a compound represented by the following structural formula described in WO02/48124

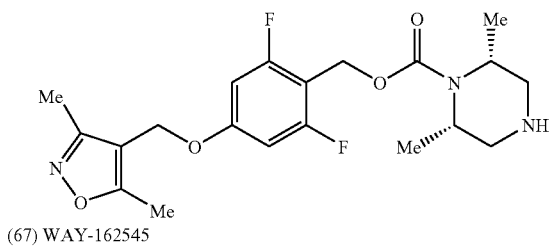

(67) WAY-162545

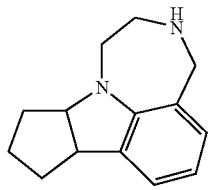

(68) WAY-163909

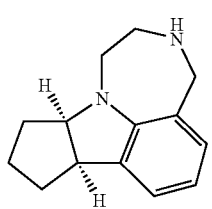

(69) IX-065

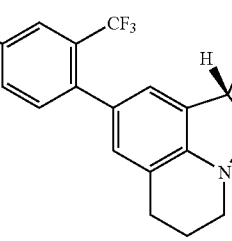

(70) A-37215

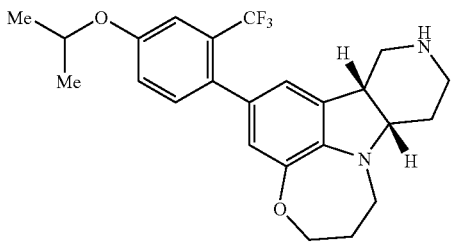

(71) a compound represented by the following structural formula described in WO05/42491

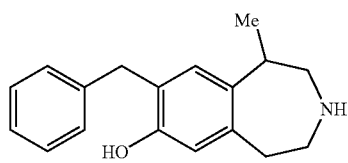 [SMILES: CC1CNCCc2cc(O)c(Cc3ccccc3)cc21]

(72) a compound represented by the following structural formula described in WO05/16902

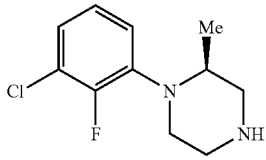 [SMILES: C[C@H]1CNCCN1c1cccc(Cl)c1F]

(73) a compound represented by the following structural formula described in WO04/99150

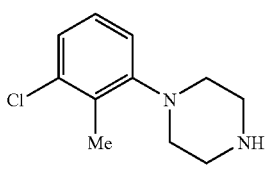 [SMILES: Cc1c(Cl)cccc1N1CCNCC1]

(74) PAL-287 and the like are preferably used.

The androgen binding site means a moiety (e.g., receptor), to which an androgen can be bound, and is not limited by the androgen receptor. The substance that stimulates the androgen binding site includes, for example, agonists (including partial agonists), partial antagonists and the like.

The substance that stimulates an androgen binding site includes, for example, testosterone

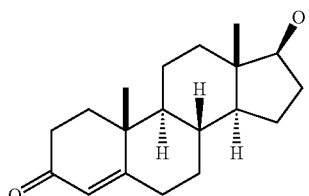

dihydrotestosterone (DHT),

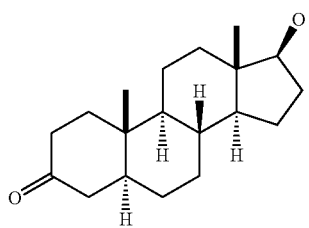

17-methyltestosterone

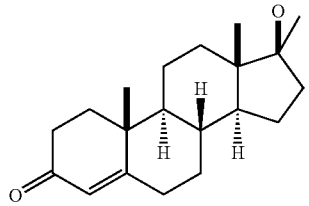

testosterone propionate and the like.

Since the substance of the present invention can increase the leak point pressure, it is useful as a safe and low toxic agent for the prophylaxis or treatment of stress urinary incontinence for mammals (e.g., mouse, rat, hamster, rabbit, cat, dog, bovine, sheep, monkey, human and the like).

The stress urinary incontinence is an involuntary leakage of urine that occurs during cough, sneeze, laugh or other physical activity that increases abdominal pressure in the absence of bladder contraction, and is different from urgency and urge urinary incontinence caused by overactive bladder.

The stress urinary incontinence is classified into normal, light, moderate, high and extremely high by the pad test (1 hr method) proposed by the International Continence Society. To be specific, the abdominal pressure after intake of 500 ml of water is increased by predetermined exercises and bodily movements for 1 hr, and the amount of incontinence during that period is measured from the weight of a pad (or paper diaper). The stress urinary incontinence is classified into normal (not more than 2 g), light (2.1 g-5.0 g), moderate (5.1 g-10.0 g), high (10.1 g-50.0 g) and extremely high (not less than 50.1 g). The substance of the present invention is useful for any type of stress urinary incontinence.

A pharmaceutical composition containing the substance of the present invention may be a solid dosage form such as powder, granule, tablet, capsule, suppository and the like, or a liquid such as syrup, emulsion, injection, suspension and the like.

The pharmaceutical composition of the present invention can be produced by a conventional method such as mixing, kneading, granulation, tableting, coating, sterilization treatment, emulsifying and the like, depending on the form of the preparation. For the production of the preparation, for example, each article of Japan Pharmacopoeia General Rules for Preparations and the like can be referred to. The pharmaceutical composition of the present invention may be formed into a sustained-release preparation containing an active ingredient and a biodegradable high molecular weight compound. The sustained-release preparation can be produced according to the method described in JP-A-9-263545.

While the content of the substance of the present invention or a salt thereof in the pharmaceutical composition of the present invention varies depending on the form of the preparation, it is generally about 0.01-100 wt %, preferably about 0.1-50 wt %, more preferably about 0.5-20 wt %, relative to the whole preparation.

When the substance of the present invention is used as the aforementioned pharmaceutical composition, it may be administered orally or parenterally as it is, or in the form of a solid agent such as powder, fine granules, granules, tablet, capsule and the like or a liquid form such as injection and the like by admixing with an appropriate pharmaceutically acceptable carrier, such as excipient (e.g., starch, lactose, sucrose, calcium carbonate, calcium phosphate and the like), binder (e.g., starch, gum arabic, carboxymethylcellulose, hydroxypropylcellulose, microcrystalline cellulose, alginic acid, gelatin, polyvinylpyrrolidone and the like), lubricant (e.g., stearic acid, magnesium stearate, calcium stearate, talc and the like), disintegrant (e.g., calcium carboxymethylcellulose, talc and the like), diluent (e.g., water for injection, saline and the like) and, where necessary, an additive (stabilizer, preservative, coloring agent, flavoring, dissolution aids, emulsifier, buffer, isotonicity agent and the like) and the like by a conventional method.

The content of the carrier in the pharmaceutical composition of the present invention is generally about 0-99.9 wt %, preferably about 10-99.9 wt %, more preferably about 10-90 wt %, relative to the whole preparation.

While the dose varies depending on the kind of the substance of the present invention or a pharmaceutically acceptable salt thereof, the level of the symptom, age, sex, body weight and sensitivity difference of the subject of administration, timing of administration, administration route, administration interval, and properties, preparation, kind and the like when prepared into a pharmaceutical composition, it is, for example, about 0.005-100 mg, preferably about 0.05-50 mg, more preferably about 0.2-30 mg, per day and per 1 kg of the body weight, as the substance of the present invention, which can be administered in 1 to 3 portions for oral administration to adult patients with stress urinary incontinence.

While the dose of the pharmaceutical composition of the present invention as a sustained-release preparation varies depending on the kind and content of the substance of the present invention, dosage form, duration of drug release, administration target animal (e.g., mammals such as human, rat, mouse, cat, dog, rabbit, bovine, swine and the like) and administration object, it is, for example, such a dose that results in the release of about 0.1 to about 100 mg of the substance of the present invention from the administered preparation in one week, for parenteral administration.

The substance of the present invention can also be used as appropriate upon mixing with other pharmaceutically active ingredient or in combination therewith.

By a concomitant use of the substance of the present invention with other pharmaceutically active ingredient, superior effects such as below can be obtained.

(1) The dose of the substance of the present invention can be reduced as compared to that in the case of a single administration thereof or that of other pharmaceutically active ingredient. More specifically, when the substance of the present invention and Clenbuterol, a β2 agonist, which is a therapeutic drug for stress urinary incontinence, are concomitantly used, the dose of Clenbuterol can be reduced as compared to a single administration thereof. Therefore, for example, side effects such as tremor and the like can be reduced.

(2) The drug to be concomitantly used with the substance of the present invention can be selected depending on the condition (mild, severe and the like) of the patients.

(3) The treatment period can be set longer by selecting other pharmaceutically active ingredient showing a different action mechanism from that of the substance of the present invention.

(4) The treatment effect can be prolonged by selecting other pharmaceutically active ingredient showing a different action mechanism from that of the substance of the present invention.

(5) By a concomitant use of the substance of the present invention with other pharmaceutically active ingredient, a synergistic effect can be obtained, and the like.

As the drug that can be mixed with or concomitantly used with the substance of the present invention (hereinafter to be abbreviated as concomitant drug), for example, the following drugs can be used.

(1) Other Drugs for Treating Stress Urinary Incontinence

Adrenaline α1 receptor agonists (e.g., ephedrine hydrochloride, midodrine hydrochloride), adrenaline β2 receptor agonists (e.g., Clenbuterol), noradrenaline uptake inhibitory substance, noradrenaline and serotonin uptake inhibitory substances (e.g., duloxetine), tricyclic antidepressants (e.g., imipramine hydrochloride), anticholinergic agent or smooth muscle stimulants (e.g., oxybutynin hydrochloride, propiverine hydrochloride, celimeverine hydrochloride), female hormone drugs (e.g., conjugated estrogen (premarin), estriol) and the like.

(2) Therapeutic Agents for Diabetes

Insulin preparations [e.g., animal insulin preparation extracted from the pancreas of bovine or swine; human insulin preparations synthesized by genetic engineering using *Escherichia coli* or yeast; zinc insulin; protamine zinc insulin; fragment or derivative of insulin (e.g., INS-1 etc.) and the like], insulin sensitizers (e.g., pioglitazone hydrochloride, troglitazone, rosiglitazone or maleate thereof, JTT-501, MCC-555, YM-440, GI-262570, KRP-297, FK-614, CS-011 etc.), α-glucosidase inhibitors (e.g., voglibose, acarbose, miglitol, emiglitate etc.), biguanides (e.g., phenformin, metformin, buformin etc.), sulfonylureas (e.g., tolbutamide, glibenclamide, gliclazide, chlorpropamide, tolazamide, acetohexamide, glyclopyramide, glimepiride etc.) and other insulin secretagogues (e.g., repaglinide, senaglinide, mitiglinide or calcium salt hydrate thereof, GLP-1, nateglinide etc.), dipeptidyl-peptidase IV inhibitors (e.g., NVP-DPP-278, PT-100, P32/98 etc.), β3 agonists (e.g., CL-316243, SR-58611-A, UL-TG-307, AJ-9677, AZ40140 etc.), amylin agonists (e.g., pramlintide etc.), phosphotyrosine phosphatase inhibitors (e.g., vanadic acid etc.), gluconeogenesis inhibitors (e.g., glycogen phosphorylase inhibitor, glucose- 6-phosphatase inhibitor, glucagon antagonist etc.), SGLT (sodium-glucose cotransporter) inhibitors (e.g., T-1095 etc.) and the like.

(3) Therapeutic Agents for Diabetic Complications

Aldose reductase inhibitors (e.g., tolrestat, epalrestat, zenarestat, zopolrestat, fidarestat (SNK-860), minalrestat (ARI-509), CT-112 etc.), neurotrophic factors (e.g., NGF, NT-3 etc.), AGE inhibitors (e.g., ALT-945, pimagedine, pyratoxanthine, N-phenacylthiazolium bromide (ALT-766), EXO-226 etc.), active oxygen scavengers (e.g., thioctic acid etc.), cerebral vasodilators (e.g., tiapuride etc.) and the like.

(4) Antihyperlipidemic Agents

Statin compounds which are cholesterol synthesis inhibitors (e.g., pravastatin, simvastatin, lovastatin, atorvastatin, fluvastatin, cerivastatin or a salt thereof (e.g., sodium salt etc.) etc.), squalene synthase inhibitors or fibrate compounds having a triglyceride lowering action (e.g., bezafibrate, clofibrate, simfibrate, clinofibrate etc.) and the like.

(5) Antihypertensive Agents

Angiotensin converting enzyme inhibitors (e.g., captopril, enalapril, delapril etc.), angiotensin II antagonists (e.g., losartan, candesartan, cilexetil etc.), calcium antagonists (e.g., manidipine, nifedipine, amlodipine, efonidipine, nicardipine etc.), clonidine and the like.

(6) Antiobesity Agents

Antiobesity agents acting on the central nervous system (e.g., dexfenfluramine, fenfluramine, phentermine, sibutramine, amfepramone, dexamphetamine, mazindol, phenylpropanolamine, clobenzorex etc.), pancreatic lipase inhibitors (e.g., orlistat etc.), β3 agonists (e.g., CL-316243, SR-58611-A, UL-TG-307, AJ-9677, AZ-40140 etc.), peptidic anorexiants (e.g., leptin, CNTF (Ciliary Neurotropic Factor) etc.), cholecystokinin agonists (e.g., lintitript, FPL-15849 etc.) and the like.

(7) Diuretic Agents

Xanthine derivatives (e.g., theobromine sodium salicylate, theobromine calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), anti-aldosterone preparations (e.g., spironolactone, triamterene etc.), carbonate dehydratase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide and the like.

(8) Chemotherapeutic Agents

Alkylating agents (e.g., cyclophosphamide, ifosfamide etc.), metabolic antagonists (e.g., methotrexate, 5-fluorouracil etc.), antitumor antibiotics (e.g., mitomycin, adriamycin etc.), plant-derived antitumor agents (e.g., vincristine, vindesine, Taxol etc.), cisplatin, carboplatin, etoposide and the like. Particularly, 5-fluorouracil derivatives (e.g., Furtulon, Neo-Furtulon and the like).

(9) Immunotherapeutic Agents

Microorganism or bacterium-derived components (e.g., muramyl dipeptide derivative, Picibanil etc.), polysaccharides having an immunoenhancing activity (e.g., lentinan, schizophyllan, krestin etc.), cytokine obtained by genetic engineering (e.g., interferon, interleukin (IL) etc.), colony stimulating factors (e.g., granulocyte colony stimulating factor, erythropoietin etc.) and the like. Particularly, IL-1, IL-2, IL-12 and the like.

(10) Pharmaceutical Agents Whose Cachexia-Improving Effect is Observed in Animal Models or Clinically Progesterone derivatives (e.g., megestrol acetate) (Journal of Clinical Oncology, vol. 12, p. 213-225, 1994), metoclopramide drugs, tetrahydrocannabinol drugs (same as those mentioned above), fat metabolism ameliorating agents (e.g., eicosapentaneoic acid etc.) (British Journal of Cancer, vol. 68, p. 314-318, 1993), growth hormone, IGF-1, or antibodies to TNF-α, LIF, IL-6 or oncostatin M, which are cachexia-inducing factors, and the like.

(11) Antiphlogistics

Steroids (e.g., dexamethasone etc.), sodium hyaluronate, cyclooxygenase inhibitors (e.g., indomethacin, ketoprofen, loxoprofen, meloxicam, ampiroxicam, celecoxib, rofecoxib etc.) and the like.

(12) Others

Glycosylation inhibitors (e.g., ALT-711 etc.), neuranagenesis stimulators (e.g., Y-128, VX853, prosaptide etc.), drugs acting on the central nervous system (e.g., antidepressants such as desipramine, amitriptyline, imipramine, fluoxetine, paroxetine, doxepin and the like), anticonvulsants (e.g., lamotrigine, carbamazepine), antiarrhythmics (e.g., mexiletine), acetylcholine receptor ligands (e.g., ABT-594), endothelin receptor antagonists (e.g., ABT-627), monoamine uptake inhibitors (e.g., tramadol), indoleamine uptake inhibitors (e.g., fluoxetine, paroxetine), anesthetic analgesics (e.g., morphine), GABA receptor agonists (e.g., gabapentin), GABA uptake inhibitors (e.g., tiagabine), $\alpha_2$ receptor agonists (e.g., clonidine), topical analgesics (e.g., capsaicin), protein kinase C inhibitors (e.g., LY-333531), antianxiety drugs (e.g., benzodiazepines), phosphodiesterase inhibitors (e.g., sildenafil), dopamine receptor agonists (e.g., apomorphine), dopamine receptor antagonists (e.g., haloperidol), serotonin receptor agonists (e.g., tandospirone citrate, sumatryptan), serotonin receptor antagonists (e.g., cyproheptadine hydrochloride, ondansetron), serotonin uptake inhibitors (e.g., fluvoxamine maleate, fluoxetine, paroxetine), sleeping pills (e.g., triazolam, zolpidem), anticholinergic agents, $\alpha_1$ receptor blockers (e.g., tamsulosin), muscle relaxants (e.g., baclofen and the like), potassium channel openers (e.g., nicorandil), calcium channel blockers (e.g., nifedipine), drugs for prophylaxis or treatment of Alzheimer's disease (e.g., donepezil, rivastigmine, galanthamine), therapeutic drugs for Parkinson's syndrome (e.g., L-DOPA), drugs for prophylaxis or treatment of multiple sclerosis (e.g., interferon β-1a), histamine $H_1$ receptor inhibitors (e.g., promethazine hydrochloride), proton pump inhibitors (e.g., lansoprazole, omeprazole), antithrombotic agents (e.g., aspirin, cilostazol), NK-2 receptor antagonist, therapeutic drug for HIV infections (saquinavir, zidovudine, lamivudine, nevirapine), therapeutic drugs for chronic obstructive pulmonary disease (salmeterol, thiotropium bromide, cilomilast) and the like.

As the anticholinergic agents, for example, atropine, scopolamine, homatropine, tropicamide, cyclopentolate, butylscopolamine bromide, propantheline bromide, methylbenactyzium bromide, mepenzolate bromide, flavoxate, pirenzepine, ipratropium bromide, trihexyphenidyl, oxybutynin, propiverine, darifenacin, tolterodine, temiverine, trospium chloride or a salt thereof (e.g., atropine sulfate, scopolamine hydrobromide, homatropine hydrobromide, cyclopentolate hydrochloride, flavoxate hydrochloride, pirenzepine hydrochloride, trihexyphenidyl hydrochloride, oxybutynin chloride, tolterodine tartrate and the like) and the like are used. Of these, oxybutynin, propiverine, darifenacin, tolterodine, temiverine, trospium chloride or a salt thereof (e.g., oxybutynin chloride, tolterodine tartrate and the like) are preferable. In addition, acetylcholinesterase inhibitors (e.g., distigmine and the like) and the like can be used.

As the NK-2 receptor antagonists, for example, piperidine derivatives such as GR159897, GR149861, SR48968 (saredutant), SR144190, YM35375, YM38336, ZD7944, L-743986, MDL105212A, ZD6021, MDL105172A, SCH205528, SCH62373, R-113281 and the like, perhydroisoindole derivatives such as RPR-106145 and the like, quinoline derivatives such as SB-414240 and the like, pyrrolopyrimidine derivatives such as ZM-253270 and the like, pseudopeptide derivatives such as MEN11420 (nepadutant), SCH217048, L-659877, PD-147714 (CAM-2291), MEN10376, S16474 and the like, as well as GR100679, DNK333, GR94800, UK-224671, MEN10376, MEN10627, or a salt thereof and the like can be mentioned.

As the pharmaceutical composition comprising the substance of the present invention and the concomitant drug include a single pharmaceutical composition containing the substance of the present invention and the concomitant drug, and the substance of the present invention and the concomitant drug separately formulated as preparations. In the following, these are generally abbreviated as the concomitant drug of the present invention.

The concomitant drug of the present invention can be formulated by mixing the substance of the present invention and a concomitant drug separately or simultaneously as they are or with a pharmaceutically acceptable carrier and the like, and then according to a method similar to that for the aforementioned pharmaceutical composition containing the substance of the present invention. The daily dose of the concomitant drug of the present invention varies depending on the level of the symptom, age, sex, body weight and sensitivity difference of the subject of administration, timing of administration, administration interval, and properties, preparation, kind of the pharmaceutical composition, the kind of the active ingredient and the like, and is not particularly limited. The dose of each of the substance of the present invention and the concomitant drug is not particularly limited as long as the side effects are not caused. It is generally about 0.005-100 mg, preferably about 0.05-50 mg, more preferably about 0.2-30 mg, for oral administration per 1 kg body weight of a mammal, which is generally administered in one to three portions a day.

For administration of the concomitant drug of the present invention, the substance of the present invention and the concomitant drug may be administered simultaneously. Alternatively, the concomitant drug may be administered first, and then the substance of the present invention may be administered, or the substance of the present invention may be administered first, and then the concomitant drug may be administered. For administration in a staggered manner, the time difference varies depending on the active ingredient to be administered, dosage form and administration method. For example, when the concomitant drug is administered first, the substance of the present invention is administered within 1 min-3 days, preferably 10 min-1 day, more preferably 15 min-1 hr, after administration of the concomitant drug. When the substance of the present invention is to be administered first, the substance of the present invention is administered, and then the concomitant drug is administered within 1 min-1 day, preferably 10 min-6 hr, more preferably 15 min-1 hr.

In the concomitant drug of the present invention simultaneously containing the substance of the present invention and the concomitant drug, the content of each of the substance of the present invention and the concomitant drug varies depending on the form of the preparation. Generally, it is about 0.01-90 wt %, preferably about 0.1-50 wt %, more preferably about 0.5-about 20 wt %, relative to the whole preparation.

The content of the carrier in the concomitant drug is generally about 0-99.8 wt %, preferably about 10-99.8 wt %, more preferably about 10-about 90 wt %, relative to the whole preparation.

In the concomitant drug of the present invention independently containing the substance of the present invention and the concomitant drug, a pharmaceutical composition containing the concomitant drug can be produced and used in the same manner as in the pharmaceutical composition containing the substance of the present invention.

The screening method of the present invention can be performed by examining the influence of a test substance on the total urinary tract resistance of an animal (e.g., non-human mammal) between administration of the test substance to the animal and without administration thereof, by the measurement of the leak point pressure.

The "leak point pressure" means the intravesical pressure at the time of urine leakage without contraction of the detrusor muscle, and shows the maximum urethral resistance capable of resisting an increase in the intravesical pressure. In the screening method of the present invention, the abdominal muscle or diaphragm or a nerve controlling them of an animal was electrostimulated to temporarily increase the abdominal pressure, the maximum intravesical pressure was measured, and the lowest values among peak intravesical pressures in the trials with incontinence was taken as the leak point pressure. A specific measurement method of the leak point pressure is described in detail in the below-mentioned Examples.

As the gender of the "animal" to be used in the present invention, female is preferable, and the species is a non-human animal such as monkey, dog, cat, rabbit, guinea pig, hamster, rat, mouse, gerbil and the like can be mentioned, and rat (Wistar, SD and the like) is most preferable.

While the age in weeks, body weight, delivery or non-delivery and the like of the "animal" to be used in the present invention are not particularly limited as long as they are applicable to the objective screening, these conditions may be appropriately changed. As the "animal" to be used in the present invention, normal animals (animals free of pathology and the like) may be used. However, those showing a low leak point pressure during increase in abdominal pressure. In rats, for example, those showing the leak point pressure of not more than about 75 mmHg are preferable. Here, the low leak point pressure preferably means a state where the nerve involved in the reflex contraction is sectioned or injured or the weight of the pelvic floor muscles and external urethral sphincter muscle is decreased. To decrease the reflex contractile force of the pelvic floor muscles and external urethral sphincter muscle, the nerve involved in the reflex urethral closing (e.g., pelvic nerve, pudendal nerve, nerve to iliococcygeus muscle/pubococcygeus muscle and the like) is physically, chemically or biologically sectioned or injured, the animal is made to deliver, the ovary is removed, vagina is mechanically expanded, diabetes is induced, a drug is administered, or they may be combined.

As the drug, for example, α-bungarotoxin, d-tubocurarine, pancuronium, decamethonium, suxamethonium and the like, which are neuromuscular junction blockers, are used.

These model animals can be produced according to a known method, for example, the method described in Urology, 1998, vol. 52, p. 143-151, Journal of Urology, 2001, vol. 166, p. 311-317.

In the screening method of the present invention, moreover, leak point pressure is measured during an abrupt and transient increase in the abdominal pressure in an animal. As a method of causing an abrupt and transient increase in the abdominal pressure, muscle contraction by electrostimulation (e.g., electrostimulation by mono or repeat rectangular pulse of duration about 0.01-about 10 milisec, preferably about 0.1-about 1 milisec, voltage about 1-about 100 V, preferably about 3-about 50 V) of the abdominal muscle or diaphragm or the nerve controlling them and the like can be mentioned.

As the test substance, a known or novel synthetic compound, a physiological active substance derived from a naturally occurring substance, peptide, protein and the like and, for example, tissue an extract, cell culture supernatant and the like of warm-blooded mammals (e.g., mouse, rat, swine, bovine, sheep, monkey, human and the like) are used.

Using this screening method, a substance that increases the leak point pressure during increment of abdominal pressure can be screened for using, as an index, the fact that the leak point pressure increases when a test substance is administered than without administration.

For example, by performing the present screening method using rats, a test substance can be evaluated to have a stress urinary incontinence-improving effect when the leak point pressure increased by about 5 $cmH_2O$, preferably not less than about 10 $cmH_2O$, more preferably not less than about 15 $cmH_2O$, with administration of the test substance as compared to the absence of administration of the test substance.

The screening method of the present invention measures the leak point pressure during an abrupt increase in abdominal pressure in an animal, and is useful for and efficiently applicable to the screening for a substance usable for the prophylaxis or treatment of stress urinary incontinence (e.g., adrenaline al receptor agonist, adrenaline β2 receptor agonist, serotonin uptake inhibitory substance, noradrenaline uptake inhibitory substance, or serotonin and noradrenaline uptake inhibitory substance and the like).

For example, in the screening method of the present invention, about 0.0001-about 1000 mg/kg (preferably about 0.001-about 100 mg/kg) of a test substance is administered to a non-human mammal, and the treatment effect of the test substance is examined with the leak point pressure as an index, whereby a drug for the prophylaxis or treatment of stress urinary incontinence can be evaluated. Here, the concept of the prophylaxis of stress urinary incontinence also includes suppression of a decrease in the urethral resistance, and the concept of the treatment of stress urinary incontinence includes improvement, suppression of progression and prophylaxis of aggravation of stress urinary incontinence. In the evaluation method of the present invention, a test substance is administered to an animal before or after the treatment for decreasing the leak point pressure, or during the measurement of leak point pressure and the like. A drug can be evaluated for the purpose of preventing or treating stress urinary incontinence according to each administration period.

While the animals to be used in the present invention may be a normal animal (animal free of pathology), for example, an animal (e.g., overweight rat (Wistar Fatty rat) and the like) showing the pathology of stress urinary incontinence, overactive bladder, benign prostatic hyperplasia, detrusor underactivity, diabetes, diabetes neuropathy, hypertension, obesity, hyperlipidemia, arteriosclerosis, gastric ulcer, asthma, chronic obstructive respiratory disease, uterus cancer, cerebrovascular disorder, brain damage, spinal cord injury and the like may be used for the measurement of the aforementioned leak point pressure. When animals showing such pathology are subjected to the aforementioned measurement of the leak point pressure, a new model animal of stress urinary incontinence can be searched for, and the measurement can be effectively applied to the screening for a pharmaceutical substance for the prophylaxis or treatment of the complications. For example, the measurement is applicable to the screening for a pharmaceutical substance effective only for the aforementioned pathology (e.g., digestive disease such as gastric ulcer and the like, and the like) and free of an influence on the stress urinary incontinence, and also applicable to the screening for the purpose of removing a test substance inducing stress urinary incontinence from a pharmaceutical substance to be selected.

Furthermore, the screening method of the present invention can be effectively applied to the screening for a pharmaceutical substance for the prophylaxis or treatment of stress urinary incontinence by applying a test substance and testing a leak point pressure increasing effect, as well as effectively applied to the screening for various pharmaceutical substances by applying a test substance and testing an influence (including aggravation, non-influence, improvement) on the urethral resistance during increase in abdominal pressure. That is, the screening method can be effectively applied to the screening for the purpose of removal of a test substance that aggravates stress urinary incontinence, from the pharmaceutical substance to be selected; selecting a test substance uninfluential on stress urinary incontinence, as a pharmaceutical substance for the prophylaxis or treatment of a disease other than stress urinary incontinence; selecting a test substance showing a stress urinary incontinence-improving effect, as a test substance for the prophylaxis or treatment of stress urinary incontinence or the complications of stress urinary incontinence with a certain kind of disease (e.g., urologic disease such as overactive bladder and the like, and the like); and the like. Different from the conventional methods, since the screening method of the present invention can evaluate the condition almost equal to the pathology, and capable of evaluation (including aggravation, non-influence, improvement) relates to stress urinary incontinence based on parametric index, rather than the judgment of the presence or absence, it can be applied as a useful evaluation system to the screening of various pharmaceutical substances for any of the aforementioned objects.

The substance obtained by the screening method of the present invention can be formed as a preparation in the same manner as in the aforementioned substance of the present invention and can be used as an agent for the prophylaxis or treatment of stress urinary incontinence.

EXAMPLES

The present invention is explained in more detail in the following by referring to Examples and Preparation Examples, which are not to be construed as limitative.

Example 1

[Experimental Method]

SD female rats (body weight 180-350 g) were anesthetized with urethane (Wako Pure Chemical Industries, Ltd.), and the spinal cord was transected at T8-9 level to eliminate the reflex voiding. During operation, halothane (Takeda Pharmaceutical Company Limited) anesthesia was added when necessary. A catheter (PE-90, Clay Adams) was inserted into the bladder and secured with a ligature, and the incised part of each of the abdominal muscle and skin was closed with sutures. The abdominal skin near the diaphragm was incised at two left and right positions to newly expose the abdominal muscle. An Evans Blue dye (Merck) solution was injected into the bladder, and the bladder volume was adjusted to 0.2-0.3 ml. The bladder catheter was connected to a pressure transducer, and the signals of the transducer were sent to a computer via an amplifier (blood pressure amplification unit AP-641G; NIHON KOHDEN) and an analog-to-digital converter (BIOPAC; MP100), and recorded on a hard disc. The data were analyzed on a computer using software (BIOPAC; AcqKnowledge). The exposed abdominal muscles were electrostimulated using an electrostimulator (SEN-3301; NIHON KODEN) and an isolator (SS-202J; NIHON KODEN), and the presence or absence of incontinence from the urethral orifice was observed. The electrostimulation was applied at a voltage of 3-50 V, duration of 0.05-0.5 milisec, and frequency 50 Hz for 1 sec, thereby gradually increasing the intravesical pressure. The peak intravesical pressure during electrostimulation of the abdominal wall was measured and, of the trials with observed incontinence, the lowest peak intravesical pressure was defined as the leak point pressure. In a certain experiment, the abdominal muscle was electrostimulated at a given stimulation intensity and, after opening the abdomen, the abdominal muscle was electrostimulated again at the same stimulation intensity. In addition, pelvic nerve, hypogastric nerve or pudendal nerve and the nerve to iliococcygeus muscle/pubococcygeus muscle were each transected bilaterally, and the effect of nerve transection was also studied.

[Results]

(1) Changes in Intravesical Pressure by Electrostimulation of Abdominal Wall in the Normal Rat The abdominal wall of the rat was electrostimulated at voltage 3-50 V, duration 0.05-0.5 milisec, frequency 50 Hz for 1 sec. As a result, the intravesical pressure increased transiently and a peak was observed during 0.3 sec to 1 sec after stimulation. Depending on the stimulus intensity, the peak intravesical pressure increased and incontinence was observed in 7/10 cases. Of the peak intravesical pressures during the stimulation that induced incontinence, the lowest trial pressure was defined as the leak point pressure. As a result, the leak point pressure of 7 cases where incontinence was observed was 50.8±2.5 cmH$_2$O. Assuming that the leak point pressure of 3 cases free of incontinence was not less than the highest intravesical pressure, the leak point pressure of 10 cases was calculated to obtain not less than 57.3±4.4 cmH$_2$O.

(2) Effect of Opening the Abdomen on the Intravesical Pressure Increase Response Due to Electrostimulation of Abdominal Wall In three rat cases, after confirmation of intravesical pressure increase response due to electrostimulation of abdominal wall, the abdomen was opened and electrostimulation was applied under the same conditions. As a result, the maximum intravesical pressure at the time of stimulation decreased from 44.5±1.2 cmH$_2$O (before opening the abdomen) to 20.3±3.4 cmH$_2$O (after opening the abdomen). From these results, it was clarified that the intravesical pressure increase response due to electrostimulation of abdominal wall was at least partly based on the abdominal pressure increase.

(3) Effects of Nerve Transection on Leak Point Pressure Due to Electrostimulation of Abdominal Wall In all cases (5 cases) of the rats whose pelvic nerve was transected bilaterally for the purpose of abolishiong the sensory information from the bladder, incontinence was observed, and a significant decrease in the leak point pressure was found (Table 1). The results suggest that the sensory information from the bladder is involved in increasing the leak point pressure during inrease in abdominal pressure. In all cases (5 cases) of the rats whose hypogasric nerve that contracts the internal urethral sphincter muscle, which is a smooth muscle, was transected bilaterally, incontinence due to electrostimulation of abdominal wall was observed. However, by comparison with sham operation rats, a decrease in the leak point pressure was not observed (Table 1).

In all cases (6 cases) of the rats whose pudendal nerve and the nerve to iliococcygeus muscle/pubococcygeus muscle controlling the external urethral sphincter muscle and pelvic floor muscles, which are skeletal muscles, were transected bilaterally (Table 1), incontinence was observed, and a significant decrease in the leak point pressure was found (Table 1). From these results, it has been clarified that a reflex contractile responses of the external urethral sphincter muscle and pelvic floor muscles, which are skeletal muscles, plays an important role for increasing the urinary tract resistance during intravesical pressure increase due to an abdominal pressure increase.

TABLE 1

Effect of bilateral transection of pelvic nerve, hypogastric nerve, or pudendal nerve and the nerve to iliococcygeus muscle/pubococcygeus muscle on leak point pressure due to electrostimulation of abdominal wall in urethane-anesthetized female rats

| | leak point pressure (cmH$_2$O) |
|---|---|
| sham operation group | 57.3 ± 4.4 |
| pelvic nerve transection group | 31.7 ± 2.7** |
| hypogastric nerve transection group | 55.0 ± 4.2 |
| Somatic nerve transection group | 39.3 ± 3.8* |

The data show mean ± SEM of 5-7 rats. The somatic nerve transection group shows a group whose pudendal nerves and the nerves to iliococcygeus muscle/pubococcygeus muscle were both bilaterally sectioned.
*P < 0.05,
**P < 0.01 vs. sham operation group (two-tailed test, Dunnett test)

Example 2

[Experimental Method]

SD female rats (body weight 180-350 g) were anesthetized with urethane (Wako Pure Chemical Industries, Ltd.), and the spinal cord was cut at T8-9 level to eliminate the reflex voiding. In addition, the nerve to the iliococcygeus muscle/pubococcygeus muscle on the one side was transected. During operation, halothane (Takeda Pharmaceutical Company Limited) anesthesia was added when necessary. A catheter (PE-90, Clay Adams) was inserted into the bladder and secured with a ligature, and the incised part of each of the abdominal muscle and skin was closed with sutures. The abdominal skin near the diaphragm was incised at two left and right positions to newly expose the abdominal muscle. An Evans Blue dye (Merck) solution was injected into the bladder, and the bladder volume was adjusted to 0.2-0.3 ml. The bladder catheter was connected to a pressure transducer, and the signals of the transducer were sent to a computer via an amplifier (blood pressure amplification unit AP-641G; NIHON KOHDEN) and an analog-to-digital converter (BIOPAC; MP100), and recorded on a hard disc. The data were analyzed on a computer using software (BIOPAC; AcqKnowledge). The exposed abdominal muscle was electrostimulated using an electrostimulator (SEN-3301; NIHON KODEN) and an isolator (SS-202J; NIHON KODEN), and the presence or absence of incontinence from the urethral orifice was observed. The electrostimulation was applied at a voltage of 3-50 V, duration of 0.05-0.5 milisec, and frequency 50 Hz for 1 sec, thereby gradually increasing the intravesical pressure. The peak intravesical pressure during stimulation of the abdominal wall was measured and, of the trials with observed incontinence, the lowest peak intravesical pressure was defined as the leak point pressure. The leak point pressure was compared before and after the duloxetine and midodrine administration. Duloxetine was dissolved in N,N-dimethyl-formamide (DMA)/polyethylene glycol 400 (PEG400) (1:1), and intravenously administered at 0.5 ml/kg. Midodrine (hydrochloride, Sigma) was dissolved in saline and intravenously administered at 1 ml/kg.

[Results]

The intravesical pressure was increased transiently by electrostimulation of the abdominal wall, and the intensity of the stimulation was gradually increased. As a result, in sham operation group, incontinence was observed in 7 out of 10 rats, and the leak point pressure of 10 cases was not less than 57.3±4.4 cmH$_2$O (previous Example). In contrast, in all cases (11 cases) of the rats whose nerve to the iliococcygeus muscle/pubococcygeus muscle on the one side was transected, incontinence was observed and the leak point pressure was 46.0±3.0 cmH$_2$O. By comparison with sham operation group, it showed a significantly low value (P=0.0436, Student's t-test). Using the rats whose nerve to the iliococcygeous muscle/pubococcygeous muscle on the one side was transected, duloxetine or midodrine showing an effect on the stress urinary incontinence was intravenously administered. Comparison of the leak point pressure before and after the administration revealed a significant increase in the leak point pressure by the both drugs (Table 2).

TABLE 2

Effects of intravenous administration of duloxetine or midodrine on the leak point pressure measured by abdominal wall-electrically stimulating method in urethane-anesthetized female rats

| | dose (mg/kg, i.v.) | number of rats | before drug administration (cmH$_2$O) | leak point pressure after drug administration (cmH$_2$O) | increase (cmH$_2$O) |
|---|---|---|---|---|---|
| solvent | — | 7 | 44.1 ± 7.1 | 43.1 ± 6.0 | 1.0 ± 1.2 |
| duloxetine | 0.3 | 5 | 45.9 ± 5.4 | 48.3 ± 7.9 | 2.4 ± 4.3 |
| | 1 | 7 | 44.9 ± 5.9 | 53.0 ± 4.8 | 8.1 ± 2.3* |
| | 3 | 6 | 48.5 ± 4.8 | 61.4 ± 3.9 | 12.9 ± 3.2* |
| | 10 | 5 | 40.0 ± 7.3 | 53.0 ± 8.8 | 13.0 ± 2.5* |
| solvent | — | 3 | 42.7 ± 7.8 | 42.1 ± 7.3 | −0.6 ± 0.6 |
| midodrine | 3 | 6 | 36.2 ± 4.8 | 39.5 ± 7.5 | 3.3 ± 4.0 |
| | 10 | 5 | 38.9 ± 4.5 | 45.1 ± 3.8 | 6.1 ± 1.4* |

The data show mean ± SEM of each group.
*P < 0.025, vs. solvent administration group (one-tailed test, Williams test).

Example 3

[Experimental Method]

SD female rats (body weight 180-350 g) were anesthetized with urethane (Wako Pure Chemical Industries, Ltd.), and the spinal cord was transected at T8-9 level to eliminate the reflex voiding. In addition, the nerve to the iliococcygeus muscle/pubococcygeus muscle on the one side was transected. During operation, halothane (Takeda Pharmaceutical Company Limited) anesthesia was added when necessary. A catheter (PE-90, Clay Adams) was inserted into the bladder and secured with a ligature, and the incised part of each of the abdominal muscle and skin was closed with sutures. The abdominal skin near the diaphragm was incised at two left and right positions to newly expose the abdominal muscle. An Evans Blue dye (Merck) solution was injected into the bladder, and the bladder volume was adjusted to 0.2-0.3 ml. The bladder catheter was connected to a pressure transducer, and the signals of the transducer were sent to a computer via an amplifier (blood pressure amplification unit AP-641G; NIHON KOHDEN) and an analog-to-digital converter (BIOPAC; MP100), and recorded on a hard disc. The data were analyzed on a computer using software (BIOPAC; Acq-Knowledge). The exposed abdominal muscle was electro-stimulated using an electrostimulator (SEN-3301; NIHON KODEN) and an isolator (SS-202J; NIHON KODEN), and the presence or absence of incontinence from the meatus urethra was observed. The electrostimulation was applied at a voltage of 2.5-50 V, duration of 0.5 milisec, and frequency 50 Hz for 1 sec, thereby gradually increasing the intravesical pressure. The peak intravesical pressure during stimulation of the abdominal wall was measured and, of the trials with observed incontinence, the lowest peak intravesical pressure was defined as the leak point pressure. Serotonin 5-HT receptor agonist, WAY-161503 (5-HT$_{2C}$ receptor agonist), WAY-163909 (5-HT$_{2C}$ receptor agonist), DOI (5-HT$_{2A/2B/2C}$ receptor agonist), mCPP (5-HT$_{2B/2C}$ receptor partial agonist), eltoprazine (5-HT$_{1A/1B/2C}$ receptor partial agonist), 8-OH-DPAT (5-HT$_{1A}$ receptor agonist), sumatryptan (5-HT$_{1B/1D}$ receptor agonist) and BW723C86 (5-HT$_{2B}$ receptor agonist) were intravenously administered, and the leak point pressure was compared before and after the administration. DOI, mCPP and eltoprazine were dissolved in saline, and other drugs were dissolved in DMA/PEG400 (1:1), and they were intravenously administered at 1 ml/kg and 0.5 mg/kg, respectively. Depending on the experiment, RS-102221 (serotonin 5-HT$_{2C}$ receptor antagonist) or SB221284 (serotonin 5-HT$_{2B/2C}$ receptor antagonist) was intravenously administered 5 min before WAY-161503 or WAY-163909 administration, and an antagonistic effect against the WAY-161503 or WAY-163909-induced increment of the leak point pressure was examined. RS-102221 and SB221284 were both dissolved in DMA/PEG400 (1:1) and intravenously administered at 0.5 ml/kg.

[Results]

Intravenous administration of WAY-161503 and WAY-163909, which are serotonin 5-HT$_{2C}$ receptor agonists, dose-dependently increased the leak point pressure, and a significant effect was afforded at a dose of not less than 0.03 mg/kg and not less than 0.1 mg/kg, respectively (Table 3). However, WAY-163907 (The Journal of Pharmacology and Experimental Therapeutics, 313, 862-869, 2005), which is an optical isomer of WAY-163909 and which is considered to be free of 5-HT$_{2C}$ receptor agonist activity, showed no effect (Table 3).

DOI (5-HT$_{2A/2B/2C}$ receptor agonist), mCPP (5-HT$_{2B/2C}$ receptor partial agonist) and eltoprazine (5-HT$_{1A/1B/2C}$ receptor partial agonist), which have a serotonin 5-HT$_{2C}$ receptor agonist activity, respectively increased the leak point pressure significantly (Table 3). However, 8-OH-DPAT, sumatryptan and BW723C86, which are 5-HT$_{1A}$ receptor agonist, 5-HT$_{1B/1D}$ receptor agonist and 5-HT$_{2B}$ receptor agonist, showed no effect (Table 3), and it has been indicated that stimulation of 5-HT$_{1A}$ receptor, 5-HT$_{1B}$ receptor, 5-HT$_{1D}$ receptor and 5-HT$_{2B}$ receptor does not affect the urinary tract resistance.

Intravenous administration of RS-102221 (serotonin 5-HT$_{2C}$ receptor antagonist) suppressed an increase in the leak point pressure by WAY-161503 (0.3 mg/kg, i.v.) or WAY-163909 (0.3 mg/kg, i.v.), where the suppression at 3 mg/kg was significant (Table 4). Moreover, SB221284 (5-HT$_{2B/2C}$ receptor antagonist) showing a serotonin 5-HT$_{2C}$ receptor antagonist activity also suppressed the leak point pressure increasing action by WAY-161503 significantly (Table 4).

TABLE 3

Effects of intravenous administration of various serotonin 5-HT receptor agonists on the leak point pressure obtained by the abdominal wall-electrically stimulating method in urethane-anesthetized female rat

| | dose (mg/kg, i.v.) | number of rats | before drug administration (cmH$_2$O) | leak point pressure after drug administration (cmH$_2$O) | increase (cmH$_2$O) |
|---|---|---|---|---|---|
| solvent | — | 11 | 49.9 ± 4.1 | 51.6 ± 4.3 | 1.7 ± 1.2 |
| WAY-161503 | 0.03 | 6 | 49.0 ± 8.0 | 58.7 ± 6.8 | 9.7 ± 2.9* |
|  | 0.1 | 6 | 46.9 ± 4.6 | 59.5 ± 4.9 | 12.6 ± 2.8* |
|  | 0.3 | 6 | 48.5 ± 5.2 | 68.1 ± 6.8 | 19.6 ± 4.4* |
|  | 1 | 6 | 49.4 ± 1.4 | 80.1 ± 2.7 | 30.7 ± 3.5* |
| solvent | — | 5 | 42.5 ± 6.4 | 42.5 ± 5.3 | 0.0 ± 2.2 |
| WAY-163909 | 0.03 | 6 | 39.5 ± 4.3 | 43.0 ± 6.3 | 3.5 ± 3.1 |
|  | 0.1 | 6 | 44.4 ± 4.5 | 55.5 ± 1.8 | 11.1 ± 3.0* |
|  | 0.3 | 6 | 41.6 ± 6.0 | 55.9 ± 8.5 | 14.4 ± 3.9* |
|  | 1 | 6 | 43.1 ± 3.4 | 67.1 ± 5.2 | 24.0 ± 3.1* |
| WAY-163907 | 3 | 4 | 52.2 ± 3.4 | 47.4 ± 4.8 | -4.8 ± 2.6 |
| solvent | — | 5 | 51.6 ± 7.0 | 49.8 ± 6.2 | -1.8 ± 1.0 |
| DOI | 0.01 | 5 | 36.4 ± 7.6 | 39.7 ± 5.2 | 3.2 ± 3.3 |
|  | 0.03 | 8 | 44.2 ± 7.2 | 50.1 ± 7.1 | 5.9 ± 1.9* |
|  | 0.1 | 5 | 44.5 ± 5.8 | 63.2 ± 5.7 | 18.7 ± 2.9* |
|  | 0.3 | 5 | 40.7 ± 8.7 | 67.9 ± 11.5 | 27.2 ± 3.9* |
| mCPP | 0.01 | 7 | 46.3 ± 5.8 | 49.1 ± 6.4 | 2.8 ± 2.1 |
|  | 0.03 | 8 | 37.7 ± 4.0 | 52.3 ± 4.3 | 14.6 ± 2.7* |
|  | 0.1 | 9 | 46.5 ± 6.1 | 59.7 ± 6.6 | 13.2 ± 2.8* |
| eltoprazine | 1 | 8 | 49.2 ± 5.2 | 55.2 ± 4.5 | 6.1 ± 1.7* |
|  | 3 | 7 | 47.4 ± 5.5 | 63.2 ± 5.6 | 15.8 ± 3.1* |
| solvent | — | 7 | 44.1 ± 7.1 | 43.1 ± 6.0 | 1.0 ± 2.2 |
| 8OH-DPAT | 0.3 | 5 | 48.5 ± 9.6 | 47.1 ± 9.4 | -1.5 ± 1.2 |
| sumatryptan | 1 | 5 | 44.2 ± 2.6 | 42.2 ± 2.0 | -2.1 ± 2.7 |
|  | 1 | 5 | 43.2 ± 8.3 | 44.9 ± 9.1 | 1.7 ± 2.4 |
|  | 3 | 6 | 52.9 ± 7.8 | 54.4 ± 7.5 | 1.5 ± 2.6 |
| BW723C86 | 3 | 7 | 46.4 ± 5.6 | 48.9 ± 4.6 | 2.5 ± 3.5 |
|  | 10 | 6 | 49.3 ± 6.5 | 48.6 ± 3.2 | -0.7 ± 3.9 |

The data show mean ± SEM.
*P < 0.025, increase in the leak point pressure was compared with that of solvent-administered group (one-tailed test, Williams test).

TABLE 4 antagonistic efefcts of serotonin 5-HT$_{2C}$ receptor antagonists on the leak point pressure increase by WAY-161503 and WAY-163909 in urethane-anesthetized female rats

| agonist | antagonist | number of cases | before drug administration (cmH$_2$O) | leak point pressure after drug administration (cmH$_2$O) | increase (cmH$_2$O) |
|---|---|---|---|---|---|
| WAY-161503 0.3 mg/kg, i.v. | solvent | 5 | 48.7 ± 5.3 | 76.6 ± 5.4 | 27.8 ± 2.8 |
| WAY-161503 0.3 mg/kg, i.v. | RS102221 1 mg/kg, i.v. | 5 | 48.3 ± 7.5 | 68.5 ± 6.1 | 20.2 ± 4.1 |
| WAY-161503 0.3 mg/kg, i.v. | RS102221 3 mg/kg, i.v. | 5 | 40.3 ± 5.5 | 50.0 ± 6.3 | 9.7 ± 2.1* |
| WAY-161503 0.3 mg/kg, i.v. | SB221284 0.1 mg/kg, i.v. | 8 | 53.3 ± 7.0 | 66.9 ± 9.8 | 13.6 ± 3.8* |
| WAY-161503 0.3 mg/kg, i.v. | SB221284 0.3 mg/kg, i.v. | 5 | 50.4 ± 6.3 | 46.8 ± 6.2 | -3.6 ± 1.4* |
| WAY-163909 0.3 mg/kg, i.v. | solvent | 5 | 43.9 ± 4.3 | 57.6 ± 4.5 | 13.7 ± 2.2 |
| WAY-163909 0.3 mg/kg, i.v. | RS102221 3 mg/kg, i.v. | 5 | 46.5 ± 5.9 | 53.0 ± 7.0 | 6.5 ± 2.4# |

The leak point pressure was measured by the abdominal wall-electrically stimulating method. The data show mean ± SEM.
*p < 0.025, increase in the leak point pressure was compared with that of solvent/WAY-161503 administered group (one-tailed test, Williams test).
# p < 0.05, increase in the leak point pressure was compared with that of the solvent/WAY-161503 administered group or solvent/WAY-163909 administered group (two-tailed test, Student's t-test).

Example 4

[Experimental Method]

SD female rats (body weight 180-350 g) were anesthetized with urethane (Wako Pure Chemical Industries, Ltd.), and halothane (Takeda Pharmaceutical Company Limited) anesthesia was added when necessary during operation.

The spinal cord was transected at T8-9 level to eliminate the reflex voiding. The lower abdomen was incised in the median line, a catheter for intravesical pressure measurement (PE-90, Clay Adams) was inserted into the bladder and secured with a ligature, and the intravesical pressure was measured via a pressure transducer. Urine was emptized in advance by bilaterally pressing the bladder with two swabs, and a 0.1% Evans blue (Merck) solution (0.4 mL) was injected into the bladder. The bladder was gradually compressed bilaterally with two swabs, and the intravesical pressure upon saline leakage from the urethral orifice was measured and defined as a leak point pressure. The measurement of the leak point pressure was repeated, and the average value of the final five stable measures was taken as the value before drug administration. Thereafter, the drug was intravenously administered, the leak point pressure was measured again 20 min later, and the value after the drug administration was determined. DOI, mCPP and eltoprazine were dissolved in saline, and other drugs were dissolved in DMA/PEG400 (1:1), and intravenously administered at 1 ml/kg and 0.5 mg/kg, respectively. Depending on the experiment, RS-102221 or SB221284 (showing serotonin 5-HT$_{2C}$ receptor antagonist activity) was administered, 5 min later, WAY-161503 or WAY-163909 was administered, leak point pressure was measured 10 min later, and a competitive assay with the action of WAY-161503 or WAY-163909 was performed. RS-102221 and SB221284 were both dissolved in DMA/PEG400 (1:1), and intravenously administered at 0.5 ml/kg.

[Results]

Duloxetine, which is a drug for stress urinary incontinence, increased the leak point pressure measured by directly compressing the bladder (Table 5). Intravenous administration of WAY-161503 and WAY-163909, which are serotonin 5-HT$_{2C}$ receptor agonists, dose-dependently increased the leak point pressure, and a significant effects were observed at a dose of not less than 0.1 mg/kg for the both (Table 5). However, WAY-163907, which is an optical isomer of WAY-163909 and which is considered to be free of 5-HT$_{2C}$ receptor agonist action, showed no effect (Table 5).

DOI (5-HT$_{2A/2B/2C}$ receptor agonist), mCPP (5-HT$_{2B/2C}$ receptor partial agonist) and eltoprazine (5-HT$_{1A/1B/2C}$ receptor partial agonist), which have a serotonin 5-HT$_{2C}$ receptor agonist activity, respectively increased the leak point pressure significantly (Table 5).

Intravenous administration of RS-102221 (serotonin 5-HT$_{2C}$ receptor antagonist) dose-dependently suppressed an increase in the leak point pressure by WAY-161503 (0.3 mg/kg, i.v.), where the suppression at 3 mg/kg was significant (Table 6).

Intravenous administration of RS-102221 dose-dependently suppressed an increase in the leak point pressure by WAY-163909, where the suppression at 3 mg/kg was significant (Table 8).

Moreover, intravenous administration of serotonin 5-HT$_{2C}$ receptor antagonist SB221284 (5-HT$_{2B/2C}$ receptor antagonist) significantly suppressed an increase in the leak point pressure by WAY-163909 (Table 6).

TABLE 5

Effects of intravenous administration of serotonin 5-HT receptor agonists and duloxetine on the leak point pressure obtained by direct compressing of the bladder in urethane-anesthetized female rat

| | | leak point pressure (cmH$_2$O) | | |
|---|---|---|---|---|
| dose (mg/kg, i.v.) | number of cases | before drug administration | after drug administration | increase |
| solvent — | 7 | 60.1 ± 4.7 | 60.9 ± 5.2 | 0.7 ± 0.7 |
| duloxetine 0.01 | 6 | 58.1 ± 6.0 | 60.5 ± 5.1 | 2.4 ± 2.6 |
| 0.03 | 8 | 61.3 ± 3.3 | 67.8 ± 2.9 | 6.5 ± 1.6* |

TABLE 5-continued

Effects of intravenous administration of serotonin 5-HT receptor agonists and duloxetine on the leak point pressure obtained by direct compressing of the bladder in urethane-anesthetized female rat

| | | | leak point pressure (cmH$_2$O) | | |
|---|---|---|---|---|---|
| | dose (mg/kg, i.v.) | number of cases | before drug administration | after drug administration | increase |
| | 0.1 | 8 | 63.3 ± 3.8 | 72.6 ± 3.4 | 9.3 ± 1.2* |
| | 0.3 | 11 | 64.5 ± 3.5 | 73.3 ± 3.9 | 8.8 ± 2.1* |
| | 1 | 11 | 61.1 ± 3.4 | 75.0 ± 4.0 | 13.9 ± 1.8* |
| solvent | — | 8 | 48.8 ± 2.6 | 50.6 ± 2.8 | 1.8 ± 1.2 |
| WAY-161503 | 0.03 | 6 | 54.9 ± 6.1 | 62.0 ± 5.8 | 7.1 ± 2.4 |
| | 0.1 | 8 | 54.7 ± 2.5 | 66.1 ± 2.8 | 11.5 ± 1.8* |
| | 0.3 | 6 | 55.7 ± 3.8 | 77.7 ± 3.6 | 22.0 ± 3.4* |
| solvent | — | 6 | 53.9 ± 3.7 | 55.6 ± 4.6 | 1.7 ± 2.8 |
| WAY-163909 | 0.03 | 5 | 66.6 ± 5.1 | 73.3 ± 3.9 | 6.6 ± 2.2 |
| | 0.1 | 5 | 64.2 ± 1.3 | 76.0 ± 2.7 | 11.8 ± 2.0* |
| | 0.3 | 6 | 52.9 ± 3.6 | 69.9 ± 3.5 | 17.0 ± 1.8* |
| | 1 | 5 | 58.4 ± 2.3 | 78.7 ± 5.7 | 20.4 ± 4.0* |
| | 3 | 5 | 52.7 ± 1.4 | 78.7 ± 4.7 | 26.0 ± 3.5* |
| solvent | — | 6 | 57.3 ± 3.9 | 59.0 ± 5.2 | 1.7 ± 2.8 |
| WAY-163907 | 3 | 5 | 55.1 ± 4.7 | 57.0 ± 5.1 | 1.9 ± 0.5 |
| solvent | — | 11 | 65.2 ± 3.6 | 65.2 ± 3.6 | 0.0 ± 1.4 |
| DOI | 0.01 | 7 | 65.7 ± 6.3 | 68.5 ± 5.7 | 2.9 ± 2.0 |
| | 0.03 | 6 | 64.9 ± 5.4 | 71.1 ± 6.7 | 6.2 ± 2.9 |
| | 0.1 | 7 | 65.2 ± 3.6 | 79.5 ± 2.6 | 14.3 ± 2.8* |
| | 0.3 | 7 | 67.0 ± 4.3 | 85.7 ± 6.0 | 18.7 ± 2.9* |
| | 1 | 7 | 60.3 ± 3.5 | 82.9 ± 3.6 | 22.6 ± 2.5* |
| mCPP | 0.003 | 5 | 62.9 ± 5.0 | 67.0 ± 5.3 | 4.1 ± 2.1 |
| | 0.01 | 9 | 63.0 ± 2.7 | 69.3 ± 3.4 | 6.3 ± 2.3* |
| | 0.03 | 8 | 62.2 ± 4.4 | 73.8 ± 7.1 | 11.6 ± 3.1* |
| | 0.1 | 8 | 63.1 ± 3.9 | 76.7 ± 4.0 | 13.6 ± 2.5* |
| | 0.3 | 6 | 65.7 ± 7.8 | 71.1 ± 7.1 | 5.4 ± 2.2 |
| eltoprazine | 1 | 6 | 68.6 ± 6.1 | 76.7 ± 4.7 | 8.0 ± 2.8* |
| | 3 | 6 | 61.1 ± 2.4 | 74.6 ± 2.3 | 13.5 ± 1.0* |

The data show mean ± SEM of each group.
*P < 0.025, vs. solvent administered group (one-tailed test, Williams test).

TABLE 6

Antagonistic effects of serotonin 5-HT$_{2c}$ receptor antagonists on the leak point pressure increase by WAY-161503 and WAY-163909 in urethane-anesthetized female rats

| | | | leak point pressure (cmH$_2$O) | | |
|---|---|---|---|---|---|
| agonist | antagonist | number of cases | before drug administration | after drug administration | increase |
| solvent | solvent | 6 | 55.0 ± 4.5 | 58.4 ± 5.4 | 3.4 ± 1.5 |
| solvent | RS102221 3 mg/kg, i.v. | 6 | 56.8 ± 5.5 | 60.7 ± 6.2 | 3.8 ± 1.9 |
| WAY-161503, 0.3 mg/kg, i.v. | solvent | 11 | 69.7 ± 3.9 | 87.1 ± 4.3 | 17.4 ± 1.9## |
| WAY-161503 0.3 mg/kg, i.v. | RS102221 1 mg/kg, i.v. | 5 | 54.7 ± 6.1 | 67.5 ± 5.4 | 12.8 ± 1.9 |
| WAY-161503 0.3 mg/kg, i.v. | RS102221 3 mg/kg, i.v. | 7 | 60.7 ± 3.3 | 70.5 ± 1.8 | 9.8 ± 2.7* |
| solvent | solvent | 8 | 58.5 ± 3.3 | 59.4 ± 3.7 | 1.0 ± 2.0 |
| solvent | RS102221 3 mg/kg, i.v. | 6 | 59.4 ± 7.0 | 59.2 ± 6.6 | −0.2 ± 2.1 |
| solvent | SB221284 0.3 mg/kg, i.v. | 7 | 64.2 ± 1.2 | 63.0 ± 2.0 | −1.2 ± 2.2 |
| WAY-163909 0.3 mg/kg, i.v. | solvent | 5 | 62.6 ± 4.2 | 77.6 ± 3.8 | 15.0 ± 1.1## |
| WAY-163909 0.3 mg/kg, i.v. | RS102221 1 mg/kg, i.v. | 5 | 62.5 ± 3.1 | 74.1 ± 3.4 | 11.6 ± 2.4 |
| WAY-163909 0.3 mg/kg, i.v. | RS102221 3 mg/kg, i.v. | 6 | 63.6 ± 3.3 | 70.9 ± 3.0 | 7.4 ± 1.4* |

TABLE 6-continued

Antagonistic effects of serotonin 5-HT$_{2C}$ receptor antagonists on the leak point pressure increase by WAY-161503 and WAY-163909 in urethane-anesthetized female rats

| agonist | antagonist | number of cases | leak point pressure (cmH$_2$O) | | |
|---|---|---|---|---|---|
| | | | before drug administration | after drug administration | increase |
| WAY-163909 0.3 mg/kg, i.v. | SB221284 0.1 mg/kg, i.v. | 5 | 53.2 ± 3.4 | 59.4 ± 3.9 | 6.2 ± 3.1* |
| WAY-163909 0.3 mg/kg, i.v. | SB221284 0.3 mg/kg, i.v. | 6 | 60.3 ± 4.0 | 60.7 ± 3.9 | 0.4 ± 1.7* |

The leak point pressure was measured by a method of directly compressing the bladder.
The data show mean ± SEM of each group.
*p < 0.025, increase in the leak point pressure was compared with that of solvent/WAY-161503 administered group or solvent/WAY-163909 administered group (one-tailed test, Williams test).
p < 0.01, increase in the leak point pressure was compared with that of solvent/solvent administered group (two-tailed test, Student's t-test).

Example 5

[Experimental Method]

SD female rats (body weight 180-350 g) were anesthetized with urethane (Wako Pure Chemical Industries, Ltd.), and the spinal cord was transected at T8-9 level to eliminate the reflex voiding.

Halothane (Takeda Pharmaceutical Company Limited) anesthesia was added when necessary during operation. After laparotomy, the bladder neck was tied with a suture thread and then a catheter (PE-90, Clay Adams) was inserted into the bladder and secured with a ligature. The other end of the bladder catheter was connected to a pressure transducer and saline storage reservoir (60 ml syringe) via a three-way stopcock. A microchip-transducer-catheter (SPR-524, Millar Instruments Inc.) was inserted from the meatus urethra. toward the bladder. Using the scale written on the catheter surface, the transducer part was set in the urethra at 12.5-15.0 mm from the urethral orifice with its side-mounted sensor facing the inner urethral surface in the 3 o'clock position.

Topical pressure changes in the urethra (hereinafter to be conveniently indicated as intraurethral pressure) measured by a microchip-transducer were input in a computer via an amplifier (blood pressure amplification unit AP-641G; NIHON KODEN) and an analog-to-digital converter (MP-100; biopack; sampled at 500 Hz) and recorded on a hard disc. The intravesical pressure was abruptly increased from 0 cmH$_2$O to 25 cmH$_2$O or 50 cmH$_2$O for 30 sec by raising the position of the saline storage reservoir by 25 cm or 50 cm, and changes in the intraurethral pressure were observed. The response of the urethra induced by the intravesical pressure increase was measured 3 times and the average of the final two measures was taken as the value before the drug administration.

The evaluation parameters were a resting intraurethral pressure and a reflex urethral contractile responses. An average intraurethral pressure per 1 sec was calculated, and the value immediately before intravesical pressure increase was taken as the resting intraurethral pressure, and the value obtained by subtracting the resting intraurethral pressure from the maximum value during intravesical pressure increase was taken as the urethral responses. After measurement of the response before drug administration, WAY-161503 (0.3 mg/kg), which is a serotonin 5-HT$_{2C}$ receptor agonist, or duloxetine (10 mg/kg) was intravenously administered, the intravesical pressure was increased again 5 min later, and the responses of the urethra were measured. The both drugs were dissolved in DMA-PEG400 (1:1), and administered at 0.5 ml/kg.

[Results]

Using rats whose reflex voiding was eliminated by spinal cord transection, the intravesical pressure was abruptly increased from 0 cmH$_2$O to 25 cmH$_2$O or 50 cmH$_2$O. As a result, an intraurethral pressure increase response (urethral response) dependent on the level of intravesical pressure increase was observed (FIG. 1).

While intravenous administration of duloxetine (10 mg/kg) enhanced the urethral contractile responses during elevation of intravesical pressure (FIG. 1, Table 7), the vehicle did not show any effect (Table 7). Intravenous administration of WAY161503 (serotonin 5-HT$_{2C}$ agonist) at a dose of 0.3 mg/kg resulted in a significant increase in the urethral contractile responses (Table 7). None of the drugs changed resting intraurethral pressure.

From these results, it has been shown that the both drugs enhance reflex urethral contractile responses (guarding reflex) during increment of intravesical pressure, and increase the urethral resistance.

TABLE 7

Drug effects on the urethral contractile responses (cmH$_2$O) induced by intravesical pressure increase in urethane-anesthetized female rats

| drug | dose (mg/kg) | increase in intravesical pressure to 25 cmH$_2$O | | increase in intravesical pressure to 50 cmH$_2$O | |
|---|---|---|---|---|---|
| | | before administration | after administration | before administration | after administration |
| solvent | — | 8.6 ± 1.0 | 6.9 ± 1.3 | 13.1 ± 1.6 | 11.2 ± 2.1 |
| duloxetine | 10 | 8.5 ± 0.5 | 11.4 ± 0.6* | 13.4 ± 2.1 | 17.8 ± 2.2** |
| WAY-161503 | 0.3 | 7.0 ± 1.4 | 11.3 ± 1.8* | 12.8 ± 2.4 | 19.2 ± 3.4** |

The data show mean ± SEM of 5 cases in each group.
*P < 0.05, ** P < 0.01, changes in the urethral contractile responses were compared with solvent group (two-tailed test, Dunnett-test).

Example 6

[Experiment Method]

SD female rats (body weight 180-350 g) were anesthetized with urethane (Wako Pure Chemical Industries, Ltd.), and the spinal cord was transected at T8-9 level to eliminate the reflex voiding.

Halothane (Takeda Pharmaceutical Company Limited) anesthesia was added when necessary during operation. After laparotomy, the bladder neck was tied with a suture thread and then a catheter (PE-90, Clay Adams) was inserted into the bladder and secured with a ligature. The other end of the bladder catheter was connected to a pressure transducer and saline storage reservoir (60 ml syringe) via a three-way cock.

Changes in the intravesical pressure measured by a transducer were input in a computer via an amplifier (blood pressure amplification unit AP-641G; NIHON KODEN) and an analog-to-digital cinverter (MP-100; biopack) and recorded on a hard disc. The intravesical pressure was raised for 90 sec by setting the saline storage reservoir at a given height, and the presence or absence of saline leakage from the urethral orifice was observed. The intravesical pressure was raised every 2.5 cmH$_2$O and, after 90 sec observation period, the intravesical pressure was once returned to 0 cmH$_2$O, after which the next step was performed. The intravesical pressure at which the saline leakage from the urethral orifice was observed was taken as the leak point pressure. The measurement of the leak point pressure was repeated and the average of the final three measures was taken as the value before the drug administration. The drug was intravenously administered, and the leak point pressure was measured again 10 min later. The drug was dissolved in DMA-PEG400 (1:1), and administered at 0.5 ml/kg.

[Results]

Duloxetine and WAY-161503 both increased the leak point pressure by the intravesical pressure-clamp method (Table 8). In addition, dihydrotestosterone (DHT), which is an androgen, increased the leak point pressure by the intravesical pressure-clamp method (Table 8). These results indicate that all of duloxetine, serotonin 5-HT$_{2C}$ receptor agonist and androgen increase the urethral resistance during elevation of intravesical pressure.

TABLE 8

Drug effects on leak point pressure (intravesical pressure-clamp method) in urethane-anesthetized female rats

|  | dose | leak point pressure (cmH$_2$O) | |
| --- | --- | --- | --- |
|  | (mg/kg, i.v.) | before drug administration | after drug administration |
| solvent | — | 26.7 ± 3.8 | 26.4 ± 3.8 |
| duloxetine | 0.001 | 36.5 ± 4.2 | 38.2 ± 3.7 |
|  | 0.01 | 37.0 ± 4.5 | 42.8 ± 4.9* |
| WAY-161503 | 0.1 | 34.9 ± 2.4 | 40.3 ± 2.5* |
|  | 1 | 34.8 ± 3.0 | 43.6 ± 3.2* |
|  | 0.01 | 33.4 ± 3.4 | 37.3 ± 3.5* |
|  | 0.03 | 34.8 ± 3.2 | 41.2 ± 3.0* |
|  | 0.1 | 33.6 ± 1.6 | 43.8 ± 2.2* |
| DHT | 0.3 | 32.1 ± 3.9 | 35.5 ± 3.9* |
|  | 1 | 35.7 ± 3.1 | 41.1 ± 3.4* |
|  | 3 | 30.5 ± 2.2 | 36.9 ± 2.1* |

The data show mean ± SEM of 5-7 rats in each group.
*P < 0.025, increase in the leak point pressure was compared with that of solvent administration administered group (one-tailed test, Williams test)

Formulation Example 1

| (1) WAY-161503 | 10 mg |
| --- | --- |
| (2) lactose | 60 mg |
| (3) cornstarch | 35 mg |
| (4) hydroxypropylmethylcellulose | 3 mg |
| (5) magnesium stearate | 2 mg |

A mixture of WAY-161503 10 mg, lactose 60 mg and cornstarch 35 mg is granulated using 10 wt % aqueous hydroxypropylmethylcellulose solution 0.03 mL (3 mg as hydroxypropylmethylcellulose) dried at 40° C. and passed through a sieve. The obtained granules are mixed with magnesium stearate 2 mg and the mixture is compressed. The obtained plain tablet is coated with glycocalyx of an aqueous suspension of saccharose, titanium dioxide, talc and gum arabic. The coated tablet is polished with bee wax to give a coated tablet.

Preparation Example 2

| (1) WAY-161503 | 10 mg |
| --- | --- |
| (2) lactose | 70 mg |
| (3) cornstarch | 50 mg |
| (4) soluble starch | 7 mg |
| (5) magnesium stearate | 3 mg |

WAY-161503 10 mg and magnesium stearate 3 mg are granulated with aqueous soluble starch solution 0.07 mL (7 mg as soluble starch), dried and mixed with lactose 70 mg and cornstarch 50 mg. The mixture is compressed to give a tablet.

Preparation Example 3

| (1) dihydrotestosterone | 10 mg |
| --- | --- |
| (2) lactose | 60 mg |
| (3) cornstarch | 35 mg |
| (4) hydroxypropylmethylcellulose | 3 mg |
| (5) magnesium stearate | 2 mg |

A mixture of dihydrotestosterone 10 mg, lactose 60 mg and cornstarch 35 mg is granulated using 10 wt % aqueous hydroxypropylmethylcellulose solution 0.03 mL (3 mg as hydroxypropylmethylcellulose) dried at 40° C. and passed through a sieve. The obtained granules are mixed with magnesium stearate 2 mg and the mixture is compressed. The obtained plain tablet is coated with glycocalyx of an aqueous suspension of saccharose, titanium dioxide, talc and gum arabic. The coated tablet is polished with bee wax to give a coated tablet.

Preparation Example 4

| (1) dihydrotestosterone | 10 mg |
| --- | --- |
| (2) lactose | 70 mg |
| (3) cornstarch | 50 mg |
| (4) soluble starch | 7 mg |
| (5) magnesium stearate | 3 mg |

Dihydrotestosterone 10 mg and magnesium stearate 3 mg are granulated with aqueous soluble starch solution 0.07 mL (7 mg as soluble starch), dried and mixed with lactose 70 mg and cornstarch 50 mg. The mixture is compressed to give a tablet.

INDUSTRIAL APPLICABILITY

Since the screening method for a drug for the prophylaxis or treatment of stress urinary incontinence of the present invention measures the urethral resistance during increment of abdominal pressure, which is abrupt and transient in accordance with the pathology, by the leak point pressure, it is superior as an in vivo evaluation system, and can be beneficially and efficiently applied to the screening for a substance to be used for the prophylaxis or treatment of stress urinary incontinence. On the other hand, it is useful as an evaluation system for testing that a substance to be used for the prophylaxis or treatment of other diseases does not induce stress urinary incontinence. Moreover, by the use of the screening method of the present invention, various pathological-physiological studies aiming at elucidation of the pathology mechanism of stress urinary incontinence, such as identification of a gene whose expression varies depending on the pathology and clarification of kinetics thereof, analysis of variation in protein expression, study of the treatment effect of gene transfer and the like on stress urinary incontinence, can be conducted efficiently with high precision.

In addition, a substance obtainable by the screening method of the present invention, for example, a substance that increases the leak point pressure during abdominal pressure increase, can be used as an agent for the prophylaxis or treatment of stress urinary incontinence.

While some of the embodiments of the present invention have been described in detail in the above, it will, however, be evident for those of ordinary skill in the art that various modifications and changes may be made to the particular embodiments shown without substantially departing from the teaching and advantages of the present invention. Such modifications and changes are encompassed in the spirit and scope of the present invention as set forth in the appended claims.

This application is based on a patent application No. 2004-245931 filed in Japan (filing date: Aug. 25, 2004, the contents of which are incorporated in full herein by this reference.

The invention claimed is:

1. A method of screening for a substance that increases a leak point pressure by about 5 cmH$_2$0 or more during an increase in abdominal pressure of an animal, which comprises:
   electrostimulating an abdominal muscle, a diaphragm, a nerve controlling the abdominal muscle or a nerve controlling the diaphragm of the animal for not more than 1 second before and after administration of at least one substance or a vehicle to cause an abrupt and transient increase in the abdominal pressure, thereby gradually increasing an intravesical pressure,
   measuring the leak point pressure during the electrostimulating,
   comparing the leak point pressure before the administration of the at least one substance or vehicle to the leak point pressure after the administration of the at least one substance or vehicle,
   further comparing the leak point pressure between a group having been administered the at least one substance and a group having been administered the vehicle, and
   selecting the substance or vehicle that increases the leak point pressure by about 5 cmH$_2$0 or more during the increase in the abdominal pressure,
   wherein the leak point pressure during the increase in the abdominal pressure of the animal results from a reflex contraction of a pelvic floor muscle and an external urethral sphincter muscle because the spinal cord of the animal has been transected at a level that is higher than that containing neurons involved in a reflex contraction of the pelvic floor muscle and the external urethral sphincter muscle in order to eliminate reflex voiding.

2. The method of claim 1, wherein the animal is female.

3. The method according to claim 1, wherein the electrostimulation is by a mono or repeat rectangular pulse of a duration of about 0.01 to about 10 ms.

4. The method according to claim 1, wherein the electrostimulation is at a voltage of about 1 to about 100 V.

5. A method of screening for a drug for the prophylaxis or treatment of stress urinary incontinence in an animal, which comprises:
   electrostimulating an abdominal muscle, a diaphragm, a nerve controlling the abdominal muscle or a nerve controlling the diaphragm of the animal for not more than 1 second before and after administration of at least one drug or a vehicle to cause an abrupt and transient increase in an abdominal pressure, thereby gradually increasing an intravesical pressure,
   measuring a leak point pressure during the electrostimulating,
   comparing the leak point pressure before the administration of the at least one drug or vehicle to the leak point pressure after the administration of the at least one drug or vehicle,
   further comparing the leak point pressure between a group having been administered the at least one drug and a group having been administered the vehicle, and
   selecting the drug or vehicle that increases the leak point pressure by about 5 cmH$_2$0 or more during the increase in the abdominal pressure,
   wherein the leak point pressure during the increase in the abdominal pressure of the animal results from a reflex contraction of a pelvic floor muscle and an external urethral sphincter muscle because the spinal cord of the animal has been transected at a level that is higher than that containing neurons involved in a reflex contraction of the pelvic floor muscle and the external urethral sphincter muscle in order to eliminate reflex voiding.

6. The method of claim 5, wherein the animal is female.

7. The method according to claim 5, wherein the electrostimulation is by a mono or repeat rectangular pulse of a duration of about 0.01 to about 10 ms.

8. The method according to claim 5, wherein the electrostimulation is at a voltage of about 1 to about 100 V.

9. A method of screening for a substance that increases a leak point pressure by 5 cmH$_2$0 or more during an increase in abdominal pressure of an animal, which comprises:
   electrostimulating an abdominal muscle, a diaphragm, a nerve controlling the abdominal muscle or a nerve controlling the diaphragm of the animal for not more than 1 second before and after administration of at least one substance or a vehicle to cause an abrupt and transient increase in the abdominal pressure, thereby gradually increasing an intravesical pressure,
   measuring the leak point pressure during the electrostimulating,
   comparing the leak point pressure before the administration of the at least one substance or vehicle to the leak point pressure after the administration of the at least one substance or vehicle,
   further comparing the leak point pressure between a group having been administered the at least one substance and a group having been administered the vehicle, and
   selecting the substance or vehicle that increases the leak point pressure by 5 cmH$_2$0 or more during increase in abdominal pressure,
   wherein the leak point pressure during the increase in the abdominal pressure of the animal results from a reflex contraction of a pelvic floor muscle and an external urethral sphincter muscle because the spinal cord of the animal has been transected at a level that is higher than that containing neurons involved in a reflex contraction of the pelvic floor muscle and the external urethral sphincter muscle in order to eliminate reflex voiding.

10. The method according to claim 9, wherein the electrostimulation is by a mono or repeat rectangular pulse of a duration of 0.01 to 10 ms.

11. The method according to claim 9, wherein the electrostimulation is at a voltage of 1 to 100 V.

12. A method of screening for a drug for the prophylaxis or treatment of stress urinary incontinence in an animal, which comprises:

electrostimulating an abdominal muscle, a diaphragm, a nerve controlling the abdominal muscle or a nerve controlling the diaphragm of the animal for not more than 1 second before and after administration of at least one drug or a vehicle to cause an abrupt and transient increase in an abdominal pressure, thereby gradually increasing an intravesical pressure, measuring a leak point pressure during the electrostimulating, comparing the leak point pressure before the administration of the at least one drug or vehicle to the leak point pressure after the administration of the at least one drug or vehicle, further comparing the leak point pressure between a group having been administered the at least one drug and a group having been administered the vehicle, and selecting the drug or vehicle that increases the leak point pressure by 5 $cmH_2O$ or more during the increase in the abdominal pressure, wherein the leak point pressure during the increase in the abdominal pressure of the animal results from a reflex contraction of a pelvic floor muscle and an external urethral sphincter muscle because the spinal cord of the animal has been transected at a level that is higher than that containing neurons involved in a reflex contraction of the pelvic floor muscle and the external urethral sphincter muscle in order to eliminate reflex voiding.

13. The method according to claim 12, wherein the electrostimulation is by a mono or repeat rectangular pulse of a duration of 0.01 to 10 ms.

14. The method according to claim 12, wherein the electrostimulation is at a voltage of 1 to 100 V.

* * * * *